US009320822B2

(12) United States Patent  
Matsumoto et al.

(10) Patent No.: US 9,320,822 B2  
(45) Date of Patent: Apr. 26, 2016

(54) POLYACRYLIC ACID (SALT) WATER-ABSORBING RESIN AND MANUFACTURING METHOD THEREFOR

(71) Applicant: NIPPON SHOKUBAI CO., LTD., Osaka (JP)

(72) Inventors: Satoshi Matsumoto, Himeji (JP); Takashi Miyamoto, Himeji (JP); Toyofumi Sakai, Himeji (JP); Yoshitake Ishii, Himeji (JP); Kunihiko Ishizaki, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 14/378,417

(22) PCT Filed: Feb. 18, 2013

(86) PCT No.: PCT/JP2013/053823  
§ 371 (c)(1),  
(2) Date: Aug. 13, 2014

(87) PCT Pub. No.: WO2013/122246  
PCT Pub. Date: Aug. 22, 2013

(65) Prior Publication Data  
US 2015/0011388 A1    Jan. 8, 2015

(30) Foreign Application Priority Data

Feb. 17, 2012 (JP) .................................. 2012-032613

(51) Int. Cl.  
| B01J 20/26 | (2006.01) |
| A61L 15/24 | (2006.01) |
| C08F 20/06 | (2006.01) |
| A61L 15/60 | (2006.01) |
| C08F 6/00 | (2006.01) |
| A61L 15/46 | (2006.01) |
| C08F 220/06 | (2006.01) |
| C08J 3/24 | (2006.01) |
| C08F 120/06 | (2006.01) |
| C08F 6/10 | (2006.01) |

(52) U.S. Cl.  
CPC .................. *A61L 15/24* (2013.01); *A61L 15/46* (2013.01); *A61L 15/60* (2013.01); *B01J 20/267* (2013.01); *C08F 6/008* (2013.01); *C08F 6/10* (2013.01); *C08F 20/06* (2013.01); *C08F 120/06* (2013.01); *C08F 220/06* (2013.01); *C08J 3/245* (2013.01); *C08J 2333/02* (2013.01)

(58) Field of Classification Search  
CPC ....................................................... B01J 20/26  
USPC ....................................................... 502/402  
See application file for complete search history.

(56) References Cited

U.S. PATENT DOCUMENTS

| 5,210,298 A | 5/1993 | Shimomura et al. |
| 6,444,744 B1 | 9/2002 | Fujimaru et al. |
| 8,765,906 B2 * | 7/2014 | Watanabe ............... C08F 6/008 |
| | | 525/329.7 |
| 9,044,525 B2 * | 6/2015 | Torii ........................ C08F 20/06 |
| 2002/0061978 A1 | 5/2002 | Hatsuda et al. |
| 2002/0120085 A1 | 8/2002 | Matsumoto et al. |
| 2004/0110914 A1 | 6/2004 | Nakahara et al. |
| 2004/0186244 A1 | 9/2004 | Hatsuda et al. |
| 2005/0209411 A1 | 9/2005 | Nestler et al. |
| 2006/0252899 A1 | 11/2006 | Himori et al. |
| 2007/0037947 A1 | 2/2007 | Hammon et al. |
| 2007/0219521 A1 | 9/2007 | Hird et al. |
| 2008/0075937 A1 | 3/2008 | Wada et al. |
| 2008/0108771 A1 | 5/2008 | Himori et al. |
| 2008/0161512 A1 | 7/2008 | Kawano et al. |
| 2008/0194863 A1 | 8/2008 | Weismantel et al. |
| 2008/0214750 A1 | 9/2008 | Stueven et al. |
| 2008/0234446 A1 | 9/2008 | Heilek et al. |
| 2008/0242816 A1 | 10/2008 | Weismantel et al. |
| 2009/0221746 A1 | 9/2009 | de Marco et al. |
| 2009/0221780 A1 | 9/2009 | Heilek et al. |
| 2009/0318885 A1 | 12/2009 | Dairoku et al. |
| 2010/0009846 A1 | 1/2010 | Ikeuchi et al. |
| 2010/0056739 A1 | 3/2010 | Funk et al. |
| 2010/0197877 A1 | 8/2010 | Funk et al. |

(Continued)

FOREIGN PATENT DOCUMENTS

| CN | 1894286 A | 1/2007 |
| JP | 2002-201290 | 7/2002 |

(Continued)

OTHER PUBLICATIONS

Chinese Office Action in corresponding CN Appln. No. 201380009785.2, dated Jun. 2, 2015, and English translation thereof.

(Continued)

*Primary Examiner* — Edward Johnson  
(74) *Attorney, Agent, or Firm* — Dickinson Wright PLLC

(57) ABSTRACT

The present invention provides a method for manufacturing a water-absorbing resin which (i) is made of acrylic acid that is suitable for mass production of water-absorbing resin and (ii) has an excellent water-absorbing property. In the method, a polyacrylic acid (salt)-based water-absorbing resin is manufactured by sequentially carrying out predetermined monomer preparing step, polymerization step, drying step, and surface crosslinking step. An acetic acid concentration in acrylic acid or the like supplied in the monomer preparing step is in a range of 300 ppm to 10000 ppm on the acrylic acid basis, and an acetic acid concentration lowering rate defined by a predetermined formula is 35% or higher.

26 Claims, No Drawings

(56) References Cited

U.S. PATENT DOCUMENTS

| | | |
|---|---|---|
| 2010/0298513 A1 | 11/2010 | Heide et al. |
| 2011/0306732 A1 | 12/2011 | Fujino et al. |
| 2012/0010372 A1 | 1/2012 | Fujino et al. |

FOREIGN PATENT DOCUMENTS

| | | |
|---|---|---|
| JP | 2006-116535 | 5/2006 |
| JP | 2008-535640 | 9/2008 |
| JP | 2011-231188 | 11/2011 |
| JP | 2012-12482 | 1/2012 |
| JP | 2012-31292 | 2/2012 |
| WO | 94/15971 | 7/1994 |
| WO | 2010/090324 | 8/2010 |
| WO | 2012/133734 | 10/2012 |

OTHER PUBLICATIONS

International Search Report and Written Opinion for PCT/JP2014/062448, dated Aug. 19, 2014.
Wampler, F., Formation of Diacrylic Acid During Acrylic Acid Storage, Plant/Operations Progress, 1988, vol. 7, No. 3, 183-189.
Buchholz, F. et al., Modern Superabsorbent Polymer Technology, WILEY-VCR, 1998, pp. 39-44.
English Translation of International Preliminary Report on Patentability for PCT/JP2013/053823, dated Aug. 28, 2014.
International Search Report for PCT/JP2013/053823, dated May 21, 2013.

* cited by examiner

POLYACRYLIC ACID (SALT) WATER-ABSORBING RESIN AND MANUFACTURING METHOD THEREFOR

TECHNICAL FIELD

The present invention relates to a polyacrylic acid (salt)-based water-absorbing resin and a method for manufacturing the polyacrylic acid (salt)-based water-absorbing resin. More specifically, the present invention relates to (i) a water-absorbing resin which is used as an absorbent body of hygiene product such as a disposable diaper and a sanitary napkin and (ii) a method for manufacturing the water-absorbing resin. Moreover, the present invention relates to a method for manufacturing, at low cost, a polyacrylic acid (salt)-based water-absorbing resin which has excellent physical properties.

BACKGROUND ART

A water-absorbing resin is recently developed as a substance having high water-absorbing property, and is widely used mainly for a disposable purpose, e.g., as an absorbent body of hygiene product such as a disposable diaper and a sanitary napkin, further, as an agriculture/horticulture water retaining agent, an industrial waterproofing agent, and the like.

Currently, various kinds of water-absorbing resin exist, and a large number of monomers and hydrophilic polymers exist as raw materials for such water-absorbing resins. Among these, a polyacrylic acid (salt)-based water-absorbing resin using acrylic acid and/or salt thereof as a monomer is most abundantly manufactured in the industry due to its high water-absorbing property.

The polyacrylic acid (salt)-based water-absorbing resin is neutralized into polyacrylic acid salt before or after polymerization of acrylic acid, and such a neutralization method and a polymerization method are disclosed in Patent Literatures 1 through 4 and Non Patent Literature 1. Moreover, Non Patent Literature 2 discloses that such acrylic acid encompasses an acrylic acid dimer.

In recent years, mass production of water-absorbing resin has been carried out in accordance with increase in demands for the water-absorbing resin. Under the circumstances, techniques have been developed for stably supplying a large amount of good-quality acrylic acid as a main raw material for the water-absorbing resin.

For example, the following techniques for preventing troubles are known, that is, a technique to remove polymers, which are generated when acrylic acid is transported or stored (Patent Literatures 5 and 6), a technique to transport acrylic acid in an aqueous solution state (Patent Literature 7), and a technique to transport acrylic acid after neutralizing the acrylic acid (Patent Literature 8).

A physical property of a water-absorbing resin is influenced by impurity in acrylic acid. Therefore, in recent years, higher-purity acrylic acid tends to be used as a raw material acid for a water-absorbing resin, in accordance with improvement in performance (i.e., physical property) of water-absorbing resin. Under the circumstances, techniques have been developed for controlling impurity in acrylic acid. Examples of such techniques encompass techniques relating to control of an acrylic acid dimer (Patent Literature 9, Non Patent Literature 1), propionic acid (Patent Literatures 10, 11), acetic acid and propionic acid (Patent Literature 12), allyl acrylate and allyl alcohol (Patent Literature 13), protoanemonin (Patent Literature 14), and furfural (Patent Literature 15).

Further, regarding trace components in the acrylic acid, a technique on a polymerization inhibitor for acrylic acid has been developed. For example, techniques are known which relate to hydroquinone and benzoquinone (Patent Literature 16), methoxyphenols (Patent Literature 17), and an N-oxyl compound and a manganese compound (Patent Literature 18).

Furthermore, techniques are known such as a technique to use acrylic acid which has been manufactured from a sustainable raw material (Patent Literature 19), a technique to use acrylic acids purchased from two or more manufacturers (Patent Literature 20), and a technique relating to countries manufacturing acrylic acid (Patent Literature 21).

Despite the improved techniques above cited, there is still room for improvement in mass production of a water-absorbing resin from acrylic acid. For example, in general, a lower impurity content in acrylic acid is considered to be better. From this, the water-absorbing resin tends to be obtained from acrylic acid that contains impurity as little as possible, as disclosed in Patent Literatures 11 through 14, etc.

However, in order to reduce the impurity content, purification of acrylic acid is carried out with a large amount of labor and cost, and this causes a problem that expansion of scale in producing water-absorbing resin from high-purity acrylic acid is greatly restricted from the viewpoint of cost, procurement of acrylic acid, and the like.

In a case where propionic acid, which is one of impurities, is controlled to be contained by a predetermined amount or more in polymerization, a water absorption capacity (CRC) of the water-absorbing resin is improved (Patent Literatures 10 and 11). However, if a large amount of the propionic acid remains after the polymerization, a resultant water-absorbing resin sometimes emits stronger unpleasant odor (acid odor).

CITATION LIST

Patent Literature

[Patent Literature 1] U.S. Pat. No. 5,210,298 (Patented date: May 11, 1993)
[Patent Literature 2] US Patent Application Publication No. 2008/242816 (Publication date: Oct. 2, 2008)
[Patent Literature 3] US Patent Application Publication No. 2009/221746 (Publication date: Sep. 3, 2009)
[Patent Literature 4] US Patent Application Publication No. 2008/194863 (Publication date: Aug. 14, 2008)
[Patent Literature 5] US Patent Application Publication No. 2009/221780 (Publication date: Sep. 3, 2009)
[Patent Literature 6] US Patent Application Publication No. 2008/234446 (Publication date: Sep. 25, 2008)
[Patent Literature 7] US Patent Application Publication No. 2010/197877 (Publication date: Aug. 5, 2010)
[Patent Literature 8] US Patent Application Publication No. 2010/056739 (Publication date: Mar. 4, 2010)
[Patent Literature 9] International Publication No. 1994/015971 (Publication date: Jul. 21, 1994)
[Patent Literature 10] US Patent Application Publication No. 2012/010372 (Publication date: Jan. 12, 2012)
[Patent Literature 11] Japanese Patent Application Publication Tokukai No. 2012-31292 (Publication date: Feb. 16, 2012)
[Patent Literature 12] US Patent Application Publication No. 2005/209411 (Publication date: Sep. 22, 2005)
[Patent Literature 13] US Patent Application Publication No. 2008/214750 (Publication date: Sep. 4, 2008)
[Patent Literature 14] US Patent Application Publication No. 2002/120085 (Publication date: Aug. 29, 2002)

[Patent Literature 15] US Patent Application Publication No. 2008/161512 (Publication date: Jul. 3, 2008)
[Patent Literature 16] U.S. Pat. No. 6,444,744 (Patented date: Sep. 3, 2002)
[Patent Literature 17] US Patent Application Publication No. 2004/110914 (Publication date: Jun. 10, 2004)
[Patent Literature 18] US Patent Application Publication No. 2010/009846 (Publication date: Jan. 14, 2010)
[Patent Literature 19] US Patent Application Publication No. 2007/219521 (Publication date: Sep. 20, 2007)
[Patent Literature 20] US Patent Application Publication No. 2010/298513 (Publication date: Nov. 25, 2010)
[Patent Literature 21] US Patent Application Publication No. 2007/037947 (Publication date: Feb. 15, 2007)

Non Patent Literature

[Non Patent Literature 1] Modern Superabsorbent Polymer Techlogoy p. 39-44, etc.
[Non Patent Literature 2] Plant Operation Progress, Vol. 7, third issue (1988) p. 183-189

SUMMARY OF INVENTION

Technical Problem

An object to be attained by the present invention is to provide a method for manufacturing a water-absorbing resin, which has an excellent water-absorbing property, by using, as a raw material, acrylic acid which is suitable for mass production of the water-absorbing resin.

Solution to Problem

In view of the problem, the inventors of the present invention have studied on a method for purifying acrylic acid. As a result, the inventors of the present invention found it possible to reduce cost in purification of acrylic acid without causing adverse influence on a water-absorbing resin and on a method for manufacturing the water-absorbing resin, by purifying acrylic acid such that an amount of acetic acid, which is one of various impurities in the acrylic acid, becomes a specific amount larger than a conventional amount. In conventional techniques, impurities in acrylic acid are separated by selecting an optimal purification method and its degree (such as the number of times) in accordance with boiling points and melting points (eutectic points) of the impurities. For example, a problem has conventionally been known that an odor (i.e., acid odor) is generated if acetic acid (boiling point: 118° C., melting point: 17° C.), which is one of impurities in acrylic acid (boiling point: 142° C., melting point: 12° C.), remains in water-absorbing resin (Patent Literature 12). However, excessive purification of acrylic acid is disadvantageous in view of cost, and sometimes causes decrease in productivity of acrylic acid. Therefore, such excessive purification of acrylic acid is disadvantageous also in view of stability in supplying a raw material (i.e., ultra-high purity acrylic acid) for the water-absorbing resin.

Under the circumstances, the inventors of the present invention focused particularly on acetic acid among various impurities in acrylic acid, and have accomplished the present invention based on the finding of a method of efficiently removing acetic acid in manufacturing a water-absorbing resin, without relying on excessive purification in preparing acrylic acid. That is, the inventors of the present invention found it possible, without causing the problem in securing the raw material acrylic acid (i.e., ultra-high purity acrylic acid), to reduce manufacturing cost and obtain a water-absorbing resin that has a high physical property and does not emit an odor by (i) using acrylic acid, which contains acetic acid by a predetermined amount or more, as a raw material for the water-absorbing resin and then (ii) removing the acetic acid in manufacturing the water-absorbing resin.

Furthermore, the inventors of the present invention have accomplished the present invention by finding it possible to reduce the odor (i.e., acid odor) generated due to acetic acid remaining in the water-absorbing resin to a level that causes no problem in the practical use, by controlling, for example, a particle diameter of the water-absorbing resin.

In order to attain the object, a method of the present invention for manufacturing a polyacrylic acid (salt)-based water-absorbing resin includes the steps of: (a) preparing a monomer aqueous solution containing acrylic acid (salt) as a main component; (b) obtaining a water-containing gel-like crosslinked polymer by carrying out aqueous solution polymerization or spray drop polymerization with the monomer aqueous solution; (c) drying the water-containing gel-like crosslinked polymer; and (d) surface-crosslinking water-absorbing resin powder obtained after the step (c), the steps (a) through (d) being carried out in this order, an acetic acid concentration in acrylic acid or an acrylic acid aqueous solution, which is supplied in the step (a), being in a range of 300 ppm to 10000 ppm (on an acrylic acid basis), and an acetic acid concentration lowering rate, which is defined by Formula 1 below, being 35% or higher:

[Math. 1]

(Acetic acid concentration lowering rate) (%)={1−(acetic acid concentration (ppm) in water-absorbing resin)/(acetic acid concentration (on acrylic acid basis) (ppm) in acrylic acid or acrylic acid aqueous solution)}×100    Formula 1 where "(acetic acid concentration (ppm) in water-absorbing resin)" is an acetic acid concentration in the polyacrylic acid (salt)-based water-absorbing resin, and "(acetic acid concentration (on acrylic acid basis) (ppm) in acrylic acid or acrylic acid aqueous solution)" is an acetic acid concentration (on the acrylic acid basis) in the acrylic acid or the acrylic acid aqueous solution which is supplied in the step (a).

Moreover, in view of the problem, the inventors of the present invention have found the water-absorbing resin, which hardly emits odor, by controlling acetic acid and other acid components remaining in the water-absorbing resin to be contained by a predetermined amount.

That is, according to a polyacrylic acid (salt)-based water-absorbing resin of the present invention, an acetic acid content (i.e., an acetic acid concentration) is in a range of 100 ppm to 7000 ppm, a propionic acid concentration (i.e., a propionic acid content) is less than 300 ppm, a residual monomer (i.e., a residual monomer concentration) is less than 500 ppm, a weight average particle diameter is 300 μm to 600 μm, and a logarithmic standard deviation ($\sigma\zeta$) of particle diameter distribution (i.e., a logarithmic standard deviation of particle size distribution) is 0.20 to 0.50.

Advantageous Effects of Invention

The present invention makes it possible to (i) reduce cost for purifying acrylic acid which is a raw material for a water-absorbing resin and (ii) use and procure a broad range of acrylic acid without restriction in purity. Accordingly, the present invention is suitable for mass production of the water-absorbing resin from the viewpoint of cost. The water-absorbing resin made by the use of the acrylic acid has excellent physical properties, and in particular it is possible to inhibit odor of the water-absorbing resin itself.

DESCRIPTION OF EMBODIMENTS

The following description will discuss details of a method for manufacturing the polyacrylic acid (salt)-based water-absorbing resin of the present invention. Note, however, that the scope of the present invention is not limited to the following descriptions, and the present invention may be appropriately modified and worked in a manner other than examples described below, to the extent of being not contrary to the purpose of the present invention. Specifically, the present invention is not limited to the embodiments below, but can be altered by a skilled person in the art within the scope of the claims. An embodiment derived from a proper combination of technical means disclosed in respective different embodiments is also encompassed in the technical scope of the present invention.

[1] Definition of Term (1-1) "Water-Absorbing Resin"

The "water-absorbing resin" of the present invention indicates a water-swelling and water-insoluble polymer gelatinizer that has the following physical properties. That is, the "water-absorbing resin" of the present invention indicates a polymer gelatinizer whose CRC (water absorption capacity without load), which is defined in ERT441.2-02 (2002) as an indicator of the "water-swelling" property, is 5 (g/g) or higher, and Ext (water soluble component), which is defined in ERT470.2-02 (2002) as an indicator of the "water-insoluble" property, is 50 wt % or less.

The water-absorbing resin can be designed as appropriate in accordance with the purpose of use, and is not limited to a particular one. The water-absorbing resin is preferably a hydrophilic cross-linked polymer which has been obtained by crosslinking and polymerizing unsaturated monomers each of which has a carboxyl group. Moreover, the water-absorbing resin is not limited to a form in which the water-absorbing resin is wholly (i.e., 100 wt %) a polymer, and can be a water-absorbing resin composition that contains an additive and the like within a range in which the above described physical properties (i.e., CRC, Ext) are satisfied.

Moreover, the water-absorbing resin of the present invention is not limited to an end product, and can be an intermediate (e.g., a dried polymer after drying or water-absorbing resin powder before surface crosslinking) obtained during manufacturing of a water-absorbing resin. As such, all of these are collectively referred to as "water-absorbing resin" in this specification.

(1-2) "Polyacrylic Acid (Salt)"

The "polyacrylic acid (salt)" of the present invention indicates a polymer that arbitrarily contains a graft component and contains, as a main component, acrylic acid and/or salt thereof (hereinafter, referred to as "acrylic acid (salt)") as a repeating unit.

Note that the "main component" indicates that an acrylic acid (salt) content (used amount) relative to entire monomers (excluding an internal crosslinking agent) used in polymerization is in a range of normally 50 mol % to 100 mol %, preferably 70 mol % to 100 mol %, more preferably 90 mol % to 100 mol %, still more preferably substantially 100 mol %. The polyacrylic acid salt as a polymer essentially contains a counter cation of a carboxyl group, preferably contains a monovalent cation, more preferably contains an alkali metal ion or an ammonium ion, particularly preferably contains sodium salt.

(1-3) "EDANA" and "ERT"

"EDANA" is an abbreviation for "European Disposables and Nonwovens Associations", and "ERT" is an abbreviation for "EDANA Recommended Test Methods" which is a European standard (which is substantially international standard) method for measuring water-absorbing resin. In the present invention, physical properties of the water-absorbing resin are measured in conformity to the ERT original copy (revised in 2002/publicly known document), unless otherwise noted.

(a) "CRC" (ERT441.2-02)

"CRC" is an abbreviation for Centrifuge Retention Capacity, and means water absorption capacity without load (also referred to as "water absorption capacity"). Specifically, "CRC" is water absorption capacity (unit; g/g) measured when 0.2 g of a water-absorbing resin in a nonwoven fabric, which water-absorbing resin has freely swollen a large excess of a 0.9 wt % of sodium chloride aqueous solution for 30 minutes, is drained by a centrifugal separator (at 250 G).

(b) "AAP" (ERT442.2-02)

"AAP" is an abbreviation for Absorption Against Pressure, and means water absorption capacity under load. Specifically, "AAP" is water absorption capacity (unit; g/g) measured when 0.9 g of a water-absorbing resin has swollen a large excess of a 0.9 wt % of sodium chloride aqueous solution for 1 hour under a load of 2.06 kPa (0.3 psi). Note that, in the present invention, the load condition is changed to 4.83 kPa (0.7 psi).

(c) "Ext" (ERT470.2-02)

"Ext" is an abbreviation for Extractables, and means a water soluble component. Specifically, "Ext" is a value (unit; wt %) obtained by measuring, by pH titration, an amount of a polymer that has been dissolved when 1.0 g of a water-absorbing resin is stirred in 200 ml of a 0.9 wt % of sodium chloride aqueous solution at 500 rpm for 16 hours.

(d) "Residual Monomers" (ERT410.2-02)

"Residual Monomers" indicates an amount of monomers that remain in a water-absorbing resin. Specifically, "Residual Monomers" is a value (unit; ppm) obtained by measuring, by high-performance liquid chromatography (HPLC), an amount of residual monomers that remain after 1.0 g of a water-absorbing resin is stirred and dissolved in 200 ml of a 0.9 wt % of sodium chloride aqueous solution at 500 rpm for 1 hour.

(e) "Moisture Content" (ERT430.2-02)

"Moisture content" is a moisture content of a water-absorbing resin. Specifically, "Moisture content" is a value (unit; wt %) calculated from a drying loss when 4.0 g of a water-absorbing resin has been dried at 105° C. for 3 hours. Note that, in the present invention, the amount of the water-absorbing resin is changed to 1.0 g and the drying temperature is changed to 180° C.

(f) "PSD" (ERT420.2-02)

"PSD" is an abbreviation for "Particle Size Distribution", and means a particle diameter distribution which is measured by sieve classification. Note that a weight average particle diameter (D50) and a particle diameter distribution range are measured in a manner disclosed in the specification of U.S. Pat. No. 7,638,570, columns 27 and 28 "(3) Mass-Average Particle Diameter (D50) and Logarithmic Standard Deviation (σζ) of Particle Diameter Distribution".

(1-4) "Liquid Permeability"

"Liquid permeability" of a water-absorbing resin indicates a flowing property of a liquid which permeates between swollen gel particles under a load or under no load, and is typically measured in terms of SFC (Saline Flow Conductivity) or GBP (Gel Bed Permeability).

"SFC (saline flow conductivity)" indicates liquid permeability of a 0.69 wt % of sodium chloride aqueous solution relative to a water-absorbing resin under a load of 2.07 kPa, and is measured in conformity to an SFC testing method disclosed in U.S. Pat. No. 5,669,894.

"GBP (gel bed permeability)" indicates liquid permeability of a 0.9 wt % of sodium chloride aqueous solution relative to a water-absorbing resin under a load or under free swell, and is measured in conformity to a GBP testing method disclosed in International Publication No. 2005/016393.

(1-5) "Acetic Acid Concentration"

In the present invention, "acetic acid concentration" indicates a concentration in a case where all acetic acids, which are contained in a monomer aqueous solution, a water-containing gel-like cross-linked polymer, and a water-absorbing resin, exist as an acid type. That is, the "acetic acid concentration" indicates a total concentration of acetic acid and acetic acid salt (on the acetic acid basis) (e.g., a total concentration of acetic acid and sodium acetate in partially neutralized sodium polyacrylate). Note that a concentration of acetic acid salt (e.g., sodium acetate having a molecular weight of 82.03) is defined as a concentration obtained by converting the weight of acetic acid salt into a weight (i.e., a molecular weight of 60.05) of acetic acid. This is because an acetic acid concentration is measured (as later described) in terms of acidity (i.e., by liquid chromatography with the use of a phosphoric acid eluting solution).

(1-6) "Acetic Acid Concentration Lowering Rate"

In the present invention, "acetic acid concentration lowering rate" is a parameter defined in Formula 1 below and is a value (unit; %) obtained from (i) an amount of acetic acid which is contained in a water-absorbing resin obtained as a product (that is, the polyacrylic acid (salt)-based water-absorbing resin of the present invention or the polyacrylic acid (salt)-based water-absorbing resin manufactured by the method of the present invention) and (ii) an amount of acetic acid which is contained in acrylic acid or an acrylic acid aqueous solution which is used as raw material acid (that is, acrylic acid or an acrylic acid aqueous solution supplied in a monomer preparing step).

[Math. 2]

(Acetic acid concentration lowering rate) (%)={1−(acetic acid concentration (ppm) in water-absorbing resin)/(acetic acid concentration (on acrylic acid basis) (ppm) in acrylic acid or acrylic acid aqueous solution)}×100     Formula 1

Here, "acetic acid concentration (ppm) in water-absorbing resin" in Formula 1 indicates an amount of acetic acid contained in a water-absorbing resin which is obtained as a product. Note that, the unit (ppm) of the amount of acetic acid herein is on the basis of weight, and an abbreviation "ppm" is used in this specification instead of "weight ppm" for convenience.

Moreover, "acetic acid concentration (on acrylic acid basis) (ppm) in acrylic acid or acrylic acid aqueous solution" indicates an acetic acid concentration (on the acrylic acid basis) in acrylic acid or an acrylic acid aqueous solution used as raw material acid. A freezing point of acrylic acid is relatively high, i.e., 12° C. From the viewpoint of ease of handling, therefore, acrylic acid is sometimes sold, transported, and stored as an acrylic acid aqueous solution whose freezing point has been decreased (e.g., as a 80 wt % of aqueous solution having a freezing point of −5.5° C.). In this case, an acetic acid concentration (ppm) in the acrylic acid aqueous solution is defined based on a weight of acrylic acid (excluding water).

How these acetic acid concentrations are measured will be described in detail in Examples.

Note that the "acetic acid concentration (on the acrylic acid basis) in acrylic acid or an acrylic acid aqueous solution used as raw material acid" is synonymous with "acetic acid concentration (on the acrylic acid basis) in acrylic acid or an acrylic acid aqueous solution supplied in monomer preparing step", and "on the acrylic acid basis" means that measurement is carried out on the basis of (i) a weight of acrylic acid used as raw material acid or (ii) a weight of acrylic acid contained in an acrylic acid aqueous solution used as raw material acid.

The acetic acid concentration "on the acrylic acid basis" can be obtained, specifically, by analyzing the acrylic acid or the acrylic acid aqueous solution, which is used as the raw material acid, with gas chromatography.

(1-7) "Acetic Acid Removing Rate"

In the present invention, "acetic acid removing rate" (unit; %) is a parameter defined by Formula 2 below and is a value that defines an amount of acetic acid removed from the water-absorbing resin in each step (unit operation). In general, an absolute amount of each of a monomer aqueous solution, a water-containing gel-like cross-linked polymer, and a dried polymer, which corresponds to a denominator, also changes in terms of weight by each of the steps, and the acetic acid removing rate is therefore calculated based on Formula 2 below by taking consideration such a change in weight.

[Math. 3]

(Acetic acid removing rate) (%)={1−(acetic acid concentration after processing) (ppm)×(weight of water-absorbing resin after processing) (g)/(acetic acid concentration before processing) (ppm)× (weight of water-absorbing resin before processing) (g)}×100     Formula 2

For example, in a case where an acetic acid removing rate in polymerization is calculated, "weight of water-absorbing resin before processing" is replaced with "weight of monomer aqueous solution", and "weight of water-absorbing resin after processing" is replaced with "weight of water-containing gel-like cross-linked polymer".

Moreover, "acetic acid concentration before processing" indicates "acetic acid concentration in monomer aqueous solution", and is a concentration of acrylic acid, which is used as raw material acid, and acetic acid are diluted with an auxiliary material (e.g., a basic compound used in neutralization, an internal crosslinking agent, or water used as a polymerization solvent). Here, the term "dilute" means a relative increase of all components which correspond to a denominator in calculating a concentration. Specifically, in a case where sodium acrylate (having a neutralization rate of 75 mol % and an average molecular weight of 88.55) is prepared from acrylic acid (having a molecular weight of 72.05), a weight of all components corresponding to a denominator is increased, and accordingly an acetic acid concentration is decreased. Note that a term "concentrate" means the opposite.

Moreover, "acetic acid concentration after processing" means "acetic acid concentration in water-containing gel-like cross-linked polymer (on the basis of an overall weight of water-containing gel-like cross-linked polymer)".

In a case where an acetic acid removing rate in a drying step is calculated, "weight of water-absorbing resin before processing" is replaced with "weight of water-containing gel-like cross-linked polymer (on the basis of an overall weight of water-containing gel-like cross-linked polymer)".

An acetic acid removing rate in a plurality of steps or in an entire process for manufacturing the water-absorbing resin can be similarly obtained by assuming the plurality of steps or the entire process for manufacturing the water-absorbing resin as one (1) step.

According to the manufacturing method in accordance with the present invention, it is preferable that acetic acid is removed by 10 wt % or more in the polymerization step and subsequent steps. That is, it is preferable to remove acetic acid, which is contained in acrylic acid or an acrylic acid aqueous solution supplied in the monomer preparing step, so that a total acetic acid removing rate defined in Formula 2 above becomes 10% or higher by the polymerization step and the subsequent steps described later.

That is, it is preferable that an amount of acetic acid in a polyacrylic acid (salt)-based water-absorbing resin, which has been obtained by the polymerization step and the subsequent steps, is preferably obtained by reducing, by the removing rate of 10% or higher, an amount of acetic acid contained in the acrylic acid or the acrylic acid aqueous solution that is supplied in the monomer preparing step.

According to the manufacturing method in accordance with the present invention, acetic acid can be efficiently removed in the polymerization step and the subsequent steps, without excessively purifying the acrylic acid that is supplied in the monomer preparing step. This allows the total acetic acid removing rate to be 10% or higher.

(1-8) Average Sphericity

A sphericity (SPHT) is defined as in Formula 3 below:

[Math. 4]

$$SPHT = \frac{4\pi A}{U^2} \qquad \text{Formula 3}$$

(where "A" is a cross-sectional area of a polymer particle, and "U" is a circumference length of the cross section of the polymer particle).

The sphericity (SPHT) is measured with a method later described. In this specification, an average sphericity is a (volume) average sphericity which is weighted with a volume of a sphere whose diameter corresponds to a minimum width of a polymer particle (here, the polyacrylic acid (salt)-based water-absorbing resin of the present invention is also encompassed in the "polymer particle").

(1-9) Others

In this specification, a range of "X to Y" means "X or more (higher) and Y or less (lower)". Moreover, "t (ton)", which is a unit of weight, means "metric ton", and "ppm" means "weight ppm" or "mass ppm", unless otherwise noted. Further, in this specification, "weight" is synonymous with "mass", "parts by weight" is synonymous with "parts by mass", and "wt %" is synonymous with "mass %". Moreover, " . . . acid (salt)" means " . . . acid and/or salt thereof", and "(meth)acrylic" means "acrylic and/or methacrylic".

Note, however, that, in this specification, acetic acid can be a salt type (i.e., acetic acid salt) in the monomer aqueous solution or in the water-absorbing resin, and the acid type acetic acid and the salt type acetic acid are collectively referred to as "acetic acid", unless otherwise noted.

[2] Method for Manufacturing Polyacrylic Acid (Salt)-Based Water-Absorbing Resin The method of the present invention for manufacturing a polyacrylic acid (salt)-based water-absorbing resin includes the steps of: (a) preparing a monomer aqueous solution containing acrylic acid (salt) as a main component; (b) obtaining a water-containing gel-like cross-linked polymer by carrying out aqueous solution polymerization or spray drop polymerization with the monomer aqueous solution; (c) drying the water-containing gel-like cross-linked polymer; and (d) surface-crosslinking water-absorbing resin powder obtained after the step (c), the steps (a) through (d) being carried out in this order, an acetic acid concentration in acrylic acid or an acrylic acid aqueous solution, which is supplied in the step (a), being in a range of 300 ppm to 10000 ppm (on an acrylic acid basis), and an acetic acid concentration lowering rate, which is defined in (1-5) above, being 35% or higher.

The acetic acid concentration lowering rate is 35% or higher, preferably 40% or higher, more preferably 50% or higher. Moreover, an upper limit of the acetic acid concentration lowering rate is preferably 80% or lower, more preferably 70% or lower, still more preferably 60% or lower.

In a case where the acetic acid concentration lowering rate is lower than 35%, a large amount of acetic acid is to remain in the water-absorbing resin, and this causes a problem of odor (acid odor). Meanwhile, in a case where the acetic acid concentration lowering rate is higher than 80%, acetic acid is to be excessively removed in manufacturing the water-absorbing resin, and this may cause decrease in productivity, increase in cost, and deterioration in physical property.

According to the present invention, methods for decreasing an acetic acid concentration are broadly classified into (i) a method in which acetic acid is diluted (i.e., dilution method) and (ii) a method in which acetic acid is removed (i.e., removal method).

(Dilution of Acetic Acid; Dilution Method)

According to the present invention, the term "dilute" means a relative increase of all components corresponding to a denominator used in calculating a concentration, as above described. That is, "dilution of acetic acid (dilution method)" indicates a method in which a weight of a water-absorbing resin, which is an end product, is increased by adding a substance to a raw material acrylic acid or a water-containing gel-like cross-linked polymer so as to lower an acetic acid concentration in the water-absorbing resin.

(Removal of Acetic Acid; Removal Method)

According to the present invention, "removal of acetic acid (removal method)" indicates a method in which acetic acid is removed outside of a system in manufacturing the water-absorbing resin. Examples of the removal method encompass washing, extracting, volatilization by heating, and the like. Among these, removal from a polymer by heating is preferable. Acetic acid (whose boiling point is 118° C.) is removed outside of the system by being heated at preferably 100° C. or higher, more preferably a temperature equal to or higher than the boiling point.

Further, in the removal from the polymer by heating, volatilization of acetic acid is facilitated by the presence of water. Therefore, it is possible to efficiently remove acetic acid by having water, in the heating, presence preferably by an excessive amount relative to acetic acid, more preferably 10 times or more relative to acetic acid in terms of weight. As the amount of water increases 100 times or more, 200 times or more, 500 times or more, in this order, (and an upper limit is 1000 times) in terms of weight relative to acetic acid, acetic acid can be removed more efficiently. Note that the "polymer" is a concept which encompasses a water-containing gel-like cross-linked polymer during and after polymerization, a dried polymer thereof, a water-absorbing resin which has been obtained in and subsequent to the drying step, and an end product.

(Reduction in Acetic Acid)

According to the present invention, the acetic acid concentration is lowered by the use of the method above described. The acetic acid concentration is lowered, preferably in and subsequent to the polymerization step, more preferably in one or more of the polymerization step, the drying step, the surface crosslinking step, and a remoistening step, still more preferably in two or more of the steps, particularly preferably in three or more of the steps, most preferably in all the four steps. Note that acetic acid removed outside of the system by the removal method and, if needed, water and acrylic acid are each preferably partially recycled as a monomer so as to be reused in the monomer aqueous solution supplied in the polymerization step.

(2-1) Purifying Step of Acrylic Acid

The method of the present invention for manufacturing polyacrylic acid (salt)-based water-absorbing resin includes, as a preliminary step, purification of acrylic acid (in a case where purified (ultra-high purity) acrylic acid is purchased, this preliminary step is carried out in a manufacturer of acrylic acid).

The purifying step is a step of purifying acrylic acid that has been obtained by a method (known method) such as hydrolysis of acrylonitrile or oxidation of propylene or acrolein, and a method for manufacturing acrylic acid and a raw material used in the manufacturing method are not limited to particular ones. According to the present invention, the method for purifying acrylic acid is exemplified by various kinds of distillation methods and crystallization methods, and the purifications are preferably carried out once or a plurality of times.

By these purification methods, at least one of impurities described below is completely removed or is reduced, and this makes it possible to inhibit, for example, defective polymerization in manufacturing the water-absorbing resin, coloring to the water-absorbing resin, and influence on a human body.

Note that general purification is carried out for the purpose of lowering a concentration of impurity as much as possible. However, such general purification sometimes causes decrease in productivity, increase in cost, and reduction in yield, because a purification device becomes huge and a large amount of energy is required for purification, e.g., for heating in distillation or cooling in crystallization.

The use of ultra-high purity acrylic acid may restrict procurement of a raw material or production, in manufacture of the water-absorbing resin.

Under the circumstances, in the purification of acrylic acid carried out for the present invention, it is preferable that acetic acid or propionic acid, which influences relatively less on the polymerization, the coloring, and the human body, is caused to remain in acrylic acid and the other impurities are preferentially reduced.

The impurities in acrylic acid vary depending on manufacturing methods and raw materials, and can be, for example, aldehydes such as benzaldehyde, acrolein, and furfural. Among these, it is preferable to reduce acrolein from the viewpoint of safety. Acrolein can be reduced by carrying out a plurality of times of purification, and it is more preferable to reduce acrolein by adding a reducing agent such as hydrazine or a hydrazine derivative. Note that contents disclosed in International Publication No. 2003/014172 can be applied to the present invention.

Impurities (e.g., acrylic acid dimer, oligomer, hydroquinone, furfural, and protoanemonin) whose boiling points are higher than that of acrylic acid can be removed by general distillation or crystallization, and it is preferable to remove such impurities by simple distillation.

Note that acrylic acid used in the present invention can be (i) obtained from an acrylic acid manufacturing plant which is adjacent to a manufacturing plant of water-absorbing resin, (ii) transported from another acrylic acid manufacturing plant, or (iii) purchased from another manufacturer. The transportation of acrylic acid can be carried out by the use of, for example, a tank truck, a tanker, or a pipeline, and any of these transportation methods is appropriately employed.

According to the present invention, it is possible to employ any of (i) acrylic acid derived from a fossil material such as propylene or propane, (ii) acrylic acid derived from a nonfossil material (biomass) such as lactic acid, 2-hydroxypropionic acid, or glycerin, and (iii) a mixture thereof.

The above listed lactic acid and 2-hydroxypropionic acid can be obtained with any of various methods for fermenting natural products, and acrylic acid can be obtained through dehydration reaction of lactic acid or 2-hydroxypropionic acid. The above listed glycerin can be obtained by saponifying or esterifying vegetable fat and oil (e.g., by-product glycerin from biodiesel), and acrylic acid can be obtained from acrolein that has been obtained through dehydration reaction of glycerin.

Such acrylic acid, which has been derived from the nonfossil material (i.e., biomass), is preferable from the viewpoint of sustainability of a raw material. However, it is necessary to carry out processes such as fermentation and dehydration in which a large amount of acetic acid is sometimes contained. That is, acrylic acid, which has been derived from the nonfossil material (i.e., biomass), had a problem in removal of acetic acid for purifying acrylic acid, as compared with vapor-phase oxidation of conventional acrylic acid which has been derived from the fossil material such as propylene or propane.

However, it is possible in the present invention to obtain the water-absorbing resin by using any of acrylic acids having a wide range of acetic acid contents. Therefore, it is possible to suitably employ not only acrylic acid derived from the fossil material but also acrylic acid derived from the nonfossil material (i.e., biomass).

That is, according to the present invention, it is possible to obtain the water-absorbing resin, in which an acetic acid concentration is sufficiently lowered (e.g., an acetic acid concentration in a range of 100 ppm to 7000 ppm), even by using any of acrylic acids having a wide range of acetic acid contents, i.e., by using acrylic acid in which the acetic acid concentration is relatively high (e.g., acrylic acid or an acrylic acid aqueous solution having an acetic acid concentration in a range of preferably 300 ppm to 10000 ppm, more preferably 1500 ppm to 10000 ppm). It is therefore possible to suitably employ acrylic acid derived from the nonfossil material (i.e., biomass).

This makes it possible to shorten, reduce, or simplify the process of removing acetic acid in manufacturing acrylic acid.

Note that methods for manufacturing acrylic acid derived from the nonfossil material (i.e., biomass) are disclosed in, for example, International Publication No. 2006/08024, International Publication No. 2007/119528, International Publication No. 2007/132926, and US Patent Application Publication No. 2007/0129570.

Moreover, methods for manufacturing water-absorbing resin from acrylic acid derived from biomass are disclosed in, for example, International Publication No. 2006/092271, International Publication No. 2006/092272, International Publication No. 2006/136336, International Publication No. 2008/023039, International Publication No. 2008/023040, and International Publication No. 2007/109128.

(Acetic Acid)

Acrylic acid obtained through purification of the present invention contains acetic acid by 300 ppm to 10000 ppm. From the viewpoint of efficiency in purification, a lower limit of the acetic acid content is preferably 400 ppm or more, more preferably 500 ppm or more, 800 ppm or more, 1000 ppm or more, 1300 ppm or more, 1500 ppm or more, in this order, and particularly preferably 2000 ppm or more. Meanwhile, an upper limit of the acetic acid concentration in acrylic acid is preferably 7000 ppm or lower, more preferably 5000 ppm or lower, still more preferably 3000 ppm or lower, from the viewpoint of odor, soluble components, water-absorbing property of the water-absorbing resin, and the like.

As such, the acetic acid concentration in acrylic acid can be selected as appropriate within the above described range, and is preferably in a range of 300 ppm to 7000 ppm, more preferably 300 ppm to 5000 ppm, 400 ppm to 5000 ppm, 500 ppm to 5000 ppm, 800 ppm to 3000 ppm, 1000 ppm to 3000 ppm, 1300 ppm to 3000 ppm, 1500 ppm to 3000 ppm, in this order, and particularly preferably 2000 ppm to 3000 ppm.

Note that, in a case where the acetic acid content (i.e., acetic acid concentration) in acrylic acid is lower than 300 ppm, the improved method of purifying acrylic acid cannot be employed and therefore excessive purification is to be carried out inefficiently. On the other hand, in a case where the acetic acid content (i.e., acetic acid concentration) is more than 10000 ppm, soluble components in a resultant water-absorbing resin are increased.

(Other Saturated Carboxylic Acid)

Acrylic acid obtained by the purification of the present invention can contain, for example, formic acid and/or propionic acid as saturated carboxylic acid in addition to acetic acid.

In a case where formic acid is contained in acrylic acid by 2 ppm to 700 ppm (1 ppm to 700 ppm in a monomer), it is possible to prevent a resultant water-absorbing resin from being colored. On the other hand, it is known that soluble components in the water-absorbing resin are increased if the formic acid content is more than 700 ppm. In general, the formic acid content is adjusted to the above described content by adding formic acid. In such a case, it is possible to apply, to the present invention, a technique disclosed in International Publication No. 2011/040575 (i.e., Patent Literature 21).

From the viewpoint of reduction of odor, a propionic acid content in acrylic acid is preferably 500 ppm or lower, more preferably 400 ppm or lower, still more preferably 300 ppm or lower (and lower limit is 0 ppm). A boiling point of propionic acid is near to the boiling point of acrylic acid, and it is therefore possible to remove propionic acid more efficiently with a crystallization method.

Note that the acetic acid concentration and the propionic acid concentration can be selected separately and arbitrarily. However, it is preferable that the acetic acid concentration is higher than the propionic acid concentration by 3 times or more, more preferably 5 times or more (and upper limit is approximately 20 times). Still more preferably, the acetic acid concentration is in a range of 1300 ppm to 10000 ppm and the propionic acid concentration is 400 ppm or lower.

According to the present invention, only acetic acid accounts for a large portion of impurities in acrylic acid after purification, and it is therefore possible to bring about the advantageous effect of the present invention.

(Methoxyphenols)

In the purification of acrylic acid of the present invention, methoxyphenols are used as a polymerization inhibitor for acrylic acid. Specifically, the methoxyphenols can be, for example, o-methoxyphenol, m-methoxyphenol, p-methoxyphenol, or a methoxyphenol that has at least one of substituent groups such as a methyl group, a t-butyl group, and a hydroxyl group. Among these, p-methoxyphenol is preferably employed.

The methoxyphenols content in acrylic acid is preferably in a range of 1 ppm to 200 ppm, more preferably 10 ppm to 160 ppm, still more preferably 50 ppm to 100 ppm, particularly preferably 50 ppm to 80 ppm.

(Other Components)

In general, various impurities are contained in acrylic acid. Acrylic acid can contain trace components below, in addition to the above described acetic acid and propionic acid, saturated organic acid such as formic acid, and methoxyphenols (in the description below, a weight of the trace components is on the basis identical with that of acetic acid contained in acrylic acid).

Concrete examples of the trace component encompass, as protoanemonin (PAN) and aldehyde contents, aliphatic aldehydes such as formaldehyde, acrolein, acetaldehyde, and propionaldehyde. Moreover, concrete examples of the trace component encompass, as unsaturated or aromatic carboxylic acid and an anhydride thereof, benzoic acid, maleic acid, maleic anhydride, phthalic anhydride, and the like. Further, examples of the trace component encompass allyl acrylate, allyl alcohol, and the like.

Moreover, as a polymerization inhibitor for acrylic acid, hydroquinone, phenothiazine, and other polymerization inhibitors may be contained in addition to or other than the above described methoxyphenols. Moreover, an organic solvent, which is used in collection and azeotropic distillation in manufacturing acrylic acid, can remain in acrylic acid. In addition to the above exemplified components, water, an acrylic acid dimer, and an acrylic acid oligomer made up of three or more monomers can be contained as impurities.

As a content of the above described other components in acrylic acid or in an acrylic acid aqueous solution, the acrylic acid dimer is contained by preferably 1000 ppm or less, more preferably 500 ppm or less, still more preferably 200 ppm or less, particularly preferably 100 ppm or less, each of protoanemonin (PAN) and an aldehyde component is contained by preferably 5 ppm or less, more preferably 1 ppm or less or detection limit or less (i.e., N.D). Allyl acrylate and allyl alcohol are contained by preferably 20 ppm or less, more preferably 10 ppm or less, still more preferably 5 ppm or less, particularly preferably 1 ppm or less or detection limit or less (i.e., N.D). The methoxyphenols content have already been described above.

According to the present invention, acrylic acid in which the acetic acid content is in a range of 300 ppm to 10000 ppm is used and an amount of the other components (i.e., the polymerization inhibitor and impurities) is controlled to the above described range. This makes it possible to obtain the water-absorbing resin which is excellent in terms of odor and physical property.

That is, according to the present invention, it is possible to manufacture the water-absorbing resin that has a higher physical property at low cost, by (i) removing or reducing acetic acid in manufacturing the water-absorbing resin and (ii) controlling an amount of the other impurities (which have a boiling point higher than that of acrylic acid) to the above described range, while reducing a load of removing acetic acid in reaction or purification of acrylic acid.

(2-2) Preparation of Monomer

This is a step of preparing an aqueous solution (monomer aqueous solution) that mainly contains acrylic acid (salt).

(Acrylic Acid)

Acrylic acid which is to be supplied in this step can be (i) a single acrylic acid that has been obtained by the above described purifying step or (ii) a mixture of the above obtained acrylic acid and another acrylic acid. Alternatively, these acrylic acids can be supplied in this step in a form of aqueous solution.

In order to simplify the purification of acrylic acid, a used amount of acrylic acid obtained by the purifying step is preferably 50 wt % or higher, more preferably 80 wt % or higher, still more preferably substantially 100 wt %, relative to a total amount of acrylic acid. Note that, in a case where, for example, an acetic acid content in acrylic acid obtained by the purifying step is high or the acetic acid content changes greatly, the acetic acid content can be diluted or stabilized to the range of 300 ppm to 10000 ppm (i.e., stabilization of acetic acid amount) by being mixed with a predetermined amount of acrylic acid whose acetic acid content is low.

In a case where a large amount of acrylic acid is evaporated in the polymerization step (later described), the evaporated acrylic acid can be (i) recycled as an acrylic acid aqueous solution by being condensed with steam generated in the polymerization step or (ii) recycled as an acrylic acid salt aqueous solution by, for example, being collected with a basic aqueous solution, in order to reduce loss. That is, it is preferable to collect acrylic acid prior to the polymerization step, particularly in the monomer preparing step.

(Monomer Used in Combination)

According to the present invention, other monomer can be used in combination with acrylic acid (salt). Examples of such a monomer encompass a water-soluble or hydrophobic unsaturated monomer. More specifically, examples of such a monomer encompass methacrylic acid, maleic acid (anhydride), fumaric acid, crotonic acid, itaconic acid, vinyl sulfonic acid, 2-(meth)acrylamide-2-methylpropane sulfonic acid, (meth)acryloxyalkane sulfonic acid and alkali metal salt thereof, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethyleneglycol(meth)acrylate, polyethyleneglycol (meth)acrylate, isobutylene, lauryl(meth)acrylate, and the like.

The water-absorbing resin of the present invention encompasses a water-absorbing resin that contains, as a copolymerization component(s), the water-soluble or hydrophobic unsaturated monomers. Moreover, by using in combination with a monomer whose acetic acid content is low, acetic acid in the water-absorbing resin is diluted.

In a case where another monomer is used in combination, a used amount of such a monomer is in a range of preferably 0 mol % to 50 mol %, more preferably 0 mol % to 30 mol %, still more preferably 0 mol % to 10 mol %, relative to acrylic acid (salt) that is used as the main component. In a case where this proportion of such a monomer is used, a water-absorbing property of the water-absorbing resin, which is obtained as a product, is further improved, and the water-absorbing resin can be manufactured at lower cost.

(Basic Composition)

The water-absorbing resin obtained in the present invention is polyacrylic acid (salt) obtained by crosslinking and polymerizing acrylic acid (salt). In order to obtain the polyacrylic acid (salt), it is preferable to neutralize acrylic acid with a basic composition (i.e., neutralizing step).

Note that, in the present invention, the term "basic composition" indicates a composition that contains a basic compound. Furthermore, according to the present invention, it is preferable that the basic composition contains, in addition to the basic compound, an iron (described below), in other words, a compound containing iron.

The basic compound can be, for example, any of alkali metal (hydrogen) carbonate, alkali metal hydroxide, ammonia, and organic amine. In order to obtain a water-absorbing resin that has a higher physical property, the basic compound is preferably strong alkaline substance, that is, alkali metal hydroxide such as sodium hydroxide, potassium hydroxide, or lithium hydroxide, particularly preferably sodium hydroxide.

Note that sodium hydroxide generally contains 0 wt % to 5 wt % of sodium carbonate and/or sodium chloride. The present invention preferably employs sodium hydroxide which contains any of these substances.

A contained amount of the iron (which is converted into $Fe_2O_3$) is preferably in a range of 0.01 ppm to 5.0 ppm, more preferably 0.1 ppm to 2.0 ppm, still more preferably 0.5 ppm to 1.0 ppm, relative to a concentration of a solid content in the basic composition (e.g., based on an amount of sodium hydroxide excluding water in a sodium hydroxide aqueous solution).

Note that an amount of Fe contained in the basic compound, the monomer aqueous solution, or the water-absorbing resin can be quantitatively determined, as Fe, with the use of, for example, ICP (inductively coupled plasma) emission spectrochemical analysis. In the ICP analysis, all components (encompassing salt of Fe and any oxidation state) are quantitatively determined as Fe. In the present invention, a total Fe content is defined by converting the amount of Fe into a weight of $Fe_2O_3$ (i.e., all the Fe components are assumed to be $Fe_2O_3$).

Examples of the iron (i.e., a compound containing iron) encompass (i) a basic compound for neutralization and other raw material and (ii) an iron which has been eluted from a metal surface (e.g., a stainless steel surface) of a device.

(Neutralizing Step)

The neutralizing step carried out in the present invention encompasses neutralization of acrylic acid that is a monomer and neutralization (i.e., post-neutralization) of a water-containing gel-like cross-linked polymer which has been obtained by crosslinking and polymerizing acrylic acid. Any of the neutralizations can be carried out with a continuous method or a batch method. In this case, the continuous method is preferable. With regard to preferable neutralization conditions such as a device, a basic composition, a temperature, and a holding time, contents disclosed in International Publication No. 2009/123197 and US Patent Application Publication No. 2008/0194863 can be preferably applied to the present invention.

Note that a neutralization rate in the present invention is preferably 10 mol % or higher and lower than 90 mol %, more preferably 40 mol % or higher and lower than 80 mol %, still more preferably 50 mol % or higher and lower than 74 mol %, particularly preferably 50 mol % or higher and lower than 72 mol %, relative to all acid groups which have been neutralized or have not been neutralized.

In a case where the neutralization rate is lower than 10 mol %, The water absorption capacity without load (CRC) may be significantly decreased. On the other hand, in a case where the neutralization rate is 90 mol % or higher, a water-absorbing resin that has high water absorption capacity under load (AAP) may not be obtained, and therefore this is not preferable. The same applies to the neutralization rate of a case where neutralization is carried out after polymerization.

According to the present invention, acrylic acid salt is any of the above described salts, preferably sodium salt. Alternatively, it is possible to use in combination with a small amount (e.g., in a range of 0 mol % to 40 mol %, preferably 0 mol % to 5 mol % relative to a total of neutralized salts) of another monovalent salt. Alternatively, neutralization can be carried out with the use of an extremely small amount (e.g., approximately 0 mol % to 5 mol %) of polyvalent metal salt. That is, in the water-absorbing resin of the present invention and the method for manufacturing the water-absorbing resin, polyacrylic acid salt whose neutralization rate falls within the above described range is employed, and particularly preferably, polyacrylic acid sodium salt is employed.

(Internal Crosslinking Agent)

Examples of an internal crosslinking agent used in the present invention encompass N,N'-methylenebisacrylamide, (poly)ethyleneglycol di(meth)acrylate, (poly)propyleneglycol di(meth)acrylate, (polyoxiethylene)trimethylolpropanetri(meth)acrylate, (polyoxiethylene)glyceroltri(meth)acrylate, trimethylolpropanedi(meth)acrylate, polyethyleneglycol di($\beta$-acryloyloxipropionate), trimethylolpropane tri($\beta$-acryloyloxipropionate), poly(meth)allyloxyalkane, polyethyleneglycol diglycidyl ether, ethyleneglycol, propyleneglycol, glycerin, butandiol, erythritol, xylitol, sorbitol, polyethyleneglycol, and the like.

One or more of these are used in the present invention. In consideration of a physical property, such as a water absorbent property, of a resultant water-absorbing resin, it is preferable to carry out polymerization with the use of (i) a compound that has two or more of polymerizable unsaturated groups, (ii) a compound that is thermally decomposed at approximately a later described drying temperature. The compound that has two or more of polymerizable unsaturated groups is, particularly, a crosslinking agent that has two or more polymerizable unsaturated groups (preferably, an allyl group, a (meth)acrylate group, particularly acrylate group) each of which has a (poly)alkylene glycol structural unit. The crosslinking agent is, for example, (poly)alkylene glycoldi(meth)acrylate or (poly)alkylene glycoltri(meth)acrylate. An alkylene glycol unit is, for example, polyethyleneglycol whose n-number is 1 to 100, preferably 6 to 50.

A used amount of the internal crosslinking agent is in a range of preferably 0.005 mol % to 2 mol %, more preferably 0.01 mol % to 1 mol %, still more preferably 0.05 mol % to 0.5 mol %, relative to a monomer. In a case where the used amount of the internal crosslinking agent falls within the above range, it is possible to obtain an intended water absorbent property.

Note that, as an alternative to the method in which crosslinking is carried out by adding an internal crosslinking agent to monomers before polymerization, the present invention can employ, for example, any of (i) a method in which an internal crosslinking agent is added to a water-containing gel-like cross-linked polymer during or after polymerization so as to carry out post-crosslinking, (ii) a method in which a radical polymerization initiator is used to carry out radical crosslinking, and (iii) a method in which an electron ray, etc., is used to carry out radiation crosslinking. It is more preferable to employ a method in which a predetermined amount of internal crosslinking agent is added to the monomers, and then polymerization is carried out so that crosslinking reaction and the polymerization are carried out simultaneously.

(Other Substance Added to Monomer)

According to the present invention, it is possible to add the following substances in addition to the above described substances in preparing a monomer aqueous solution. Specifically, in order to improve physical properties of the water-absorbing resin, a water-soluble resin or a water-absorbing resin can be added by preferably 0 wt % to 50 wt %, more preferably 0 wt % to 20 wt %, and/or various kinds of foaming agents (such as carbonate, azo compound, and gas bubbles), a surfactant, a chelating agent, a chain transfer agent, and the like can be added by preferably 0 wt % to 5 wt %, more preferably 0 wt % to 1 wt %.

Note that, by using the water-soluble resin or the water-absorbing resin, a graft polymer or a water-absorbing resin composition (e.g., a starch-acrylic acid polymer or a PVA-acrylic acid polymer) is generated. In the present invention, these polymers and the water-absorbing resin composition are collectively referred to as "polyacrylic acid (salt)-based water-absorbing resin".

(Water)

In a monomer preparing step, a monomer aqueous solution is prepared by mixing the above described substances. In this case, a concentration of a monomer component in the monomer aqueous solution is not limited to a particular one. Note, however, that the concentration is in a range of preferably 10 wt % to 70 wt %, more preferably 15 wt % to 65 wt %, still more preferably 30 wt % to 55 wt %, from the viewpoint of physical property of the water-absorbing resin. Note that the concentration is determined as appropriate in accordance with a temperature of the aqueous solution and a composition of the monomer. It is preferable that the concentration falling within the above range is not higher than a saturating concentration. Alternatively, it is possible to carry out polymerization with a monomer slurry (e.g., a state in which solid sodium acrylate is partially dispersed in a monomer aqueous solution) whose monomer concentration is higher than a concentration of a saturated aqueous solution of a monomer (e.g., acrylic acid salt).

In a case where polymerization is carried out with an aqueous solution, a solvent, which is not water, can be used in combination with water as appropriate. In such a case, a type of the solvent used is not limited to a particular one. A used amount of the solvent, which is not water, is in a range of preferably 0 wt % to 10 wt %, more preferably 0 wt % to 5 wt %, relative to the water.

Note that the "concentration of monomer component" is obtained based on the following formula: i.e., (weight of monomer component)/(weight of monomer aqueous solution)×100 (wt %). The monomer aqueous solution does not include the graft component and the water-absorbing resin.

(2-3) Polymerization Step

In this step, a water-containing gel-like cross-linked polymer (hereinafter, also referred to as "hydrogel") is obtained by polymerizing an acrylic acid (salt)-based monomer aqueous solution obtained in the monomer preparing step.

(Removal of Acetic Acid)

The present invention can employ a known polymerization method such as aqueous solution polymerization, spray drop polymerization, or slurry polymerization.

Among these, the aqueous solution polymerization is most preferable. In the aqueous solution polymerization, it is easy to control a polymerization temperature and a polymerization time, and it is possible to secure time required to evaporate acetic acid. This makes it possible to most efficiently remove acetic acid in the polymerization step. Further, the aqueous solution polymerization can be carried out with a continuous method or a batch method. Any of the following polymerizations (i.e., first method and second method) is preferably carried out, and at least part of acetic acid is removed in the polymerization step.

An acetic acid removing rate (which is defined by Formula 2 above) in the polymerization step is preferably 5% or higher, more preferably 10% or higher, still more preferably 15% or higher, particularly preferably 20% or higher. An upper limit is not limited to a particular one, and is preferably 70% or lower, more preferably 50% or lower, from the viewpoint of productivity.

Note that, if reverse phase suspension polymerization is employed in which polymerization is carried out by dispersing a monomer aqueous solution in a hydrophobic organic solvent, relatively strong hydrophobic solvent odor may remain in addition to acid odor in a resultant polyacrylic acid (salt)-based water-absorbing resin. Therefore, the reverse phase suspension polymerization is not encompassed in the polymerizations that can be employed in the present invention. Moreover, in the reverse phase suspension polymerization, a dispersing agent and a surfactant are required in the polymerization, and consequently surface tension of an absorbed liquid (e.g., urine), which makes contact with the resultant water-absorbing resin, may be excessively decreased and therefore a re-wet from the absorbent body may be increased.

(First Method)

According to the present invention, acetic acid is removed with a first method in the polymerization step. The first method is foaming polymerization or grain refining polymerization in which a concentration of solid content of a monomer aqueous solution, which is in a range of 30 wt % to 55 wt %, is increased (i.e., a degree of increase in solid content defined by Formula 4 below) in the polymerization by preferably 1 wt % to 15 wt %, more preferably 2 wt % to 14 wt %, still more preferably 3 wt % to 13 wt %, particularly preferably 4 wt % to 12 wt %, most preferably 5 wt % to 11 wt %.

By the polymerization, at least part of acetic acid contained in the monomer aqueous solution is removed together with water. By controlling the degree of increase in solid content to fall within the above described range, the physical property of the water-absorbing resin is improved and an amount of residual acetic acid is decreased.

Note that the degree of increase in solid content is obtained by the following Formula 4.

[Math. 5]

(Degree of increase in solid content) (wt %)=(concentration of solid content in hydrogel after polymerization)−(concentration of solid content in monomer aqueous solution)  Formula 4

In Formula 4, "concentration of solid content in monomer aqueous solution" indicates a ratio (wt %) of a total amount of monomers, a crosslinking agent, a graft component, a water-absorbing resin, and the other solid substances (e.g., water-insoluble fine particles) relative to an amount of all the components in the polymerization system including the monomer aqueous solution, the graft component, the water-absorbing resin, and the other solid substances (e.g., water-insoluble fine particles).

In this case, the foaming polymerization or the grain refining polymerization is preferable as the polymerization method in which the solid content is increased. In the foaming polymerization, as above described, polymerization is carried out on a monomer aqueous solution to which a foaming agent (e.g., carbonate, azo compound, and gas bubbles) has been added. Alternatively, the foaming polymerization can be carried out by generating gas bubbles by boiling a monomer aqueous solution in polymerization, in particular, by boiling a monomer aqueous solution immediately after starting polymerization (preferably within 5 minutes, more preferably within 3 minutes). In the grain refining polymerization, polymerization and gel-crushing are carried out simultaneously as with kneader polymerization so that a hydrogel is obtained whose particle diameter is preferably 3 mm or smaller, more preferably 1 mm or smaller.

More preferably, the grain refining polymerization is continuous kneader polymerization which is carried out under airflow, and a hydrogel is finely grained to an intended range, preferably to a range described in (2-4) below by controlling a rotation speed and rotation time of a kneader and an amount of internal crosslinking agent, etc. in the polymerization. By employing any of the polymerization methods (i.e., foaming polymerization and grain refining polymerization), a specific surface area ($cm^2/g$) of the hydrogel is increased, and it is therefore possible to more efficiently remove acetic acid (by volatilization) in or subsequent to the polymerization step.

When the solid content increases, acrylic acid (whose boiling point is 142° C.) may also be evaporated together with water and acetic acid. In such a case, in order to reduce loss of acrylic acid, it is preferable to recycle the evaporated components as an acrylic acid (salt) aqueous solution by condensing or collecting the evaporated components in a step before the polymerization step.

Note that an acetic acid concentration in acrylic acid or the acrylic acid aqueous solution may be increased by the collection, and it is therefore preferable to collect evaporated components which include at least 1 wt % of acrylic acid.

(Second Method)

According to the present invention, acetic acid is removed with a second method in the polymerization step. In the second method, a monomer aqueous solution whose concentration of solid content is lower than 30 wt % is polymerized, in other words, unneutralized or partially neutralized acrylic acid, whose neutralization rate is 30 mol % or lower, is polymerized. By the polymerization, at least part of acetic acid contained in the monomer aqueous solution is removed. The second method preferably further includes post-neutralization in which a hydrogel is neutralized in and/or subsequent to the polymerization step.

Note that in a case where acrylic acid salt, which has been neutralized, is polymerized, acetic acid in acrylic acid is also neutralized to be acetic acid salt (e.g., sodium acetate). In this case, sodium acetate is not volatilized because a boiling point of acetic acid is 118° C. while sodium acetate is decomposed at 324° C.

Under the circumstances, it is preferable to remove acetic acid in the polymerization step with the use of acrylic acid which is hardly neutralized or is not neutralized. This makes it possible to easily volatilize acetic acid in the polymerization.

(Polymerization Temperature and Airflow)

In a case where a polymerization method other than the first method and the second method is employed, acetic acid is volatilized in polymerization at a polymerization temperature (i.e., highest achieving temperature) of preferably 95° C. or higher, more preferably 100° C. or higher, still more preferably 105° C. or higher. Moreover, from the viewpoint of a physical property of a resultant water-absorbing resin, an upper limit of the polymerization temperature is preferably 140° C. or lower, more preferably 130° C. or lower. From the viewpoint of removal of acetic acid, it is preferable that the polymerization temperature (highest achieving temperature) is achieved as quickly as possible, and concretely, preferably 20 minutes or shorter, more preferably 5 minutes or shorter, still more preferably 3 minutes or shorter.

It is preferable that polymerization is carried out in the presence of an upper part space (i.e., gas), more preferably under airflow, still more preferably under reduced pressure.

The airflow or the reduced pressure is preferable because it becomes easier to remove acetic acid.

(Polymerization Initiator)

A polymerization initiator used in the present invention is selected as appropriate in accordance with a polymerization method or the like and is not limited to a particular one. Examples of the polymerization initiator encompass a pyrolytic polymerization initiator, a photolytic polymerization initiator, a redox polymerization initiator that contains a reducing agent for facilitating decomposition of any of those polymerization initiators, and the like.

Specifically, examples of the polymerization initiator encompass persulfate such as potassium persulfate, ammonium persulfate, and sodium persulfate; hydroperoxide such as t-butylhydroperoxide and hydrogen peroxide; an azo compound such as 2,2'-azobis(2-amidinopropane)dihydrochloride; 2-hydroxy-1-phenylpropane-1-one, benzoin methylether, and the like.

Examples of the reducing agent encompass (bi)sulfite (salt) such as sodium sulfite and sodium hydrogen sulfite; reducing metal (salt) such as L-ascorbic acid (salt) and ferrous salt; amines; and the like.

A used amount of the polymerization initiator is in a range of preferably 0.001 mol % to 1 mol %, more preferably 0.001 mol % to 0.5 mol %, relative to monomers. A used amount of the reducing agent is preferably in a range of 0.0001 mol % to 0.02 mol %, relative to monomers.

Alternatively, polymerization reaction can be carried out by irradiation of active energy ray such as radial ray, electron ray, or ultraviolet ray instead of using the polymerization initiator. Alternatively, the active energy ray and the polymerization initiator can be used in combination. Further, it is preferable to add a chelating agent (later described) to a monomer aqueous solution before or during polymerization, and to polymerize the monomer aqueous solution, because the advantageous effects of the present invention can be further brought about.

(Polymerization Method)

The polymerization method employed in the present invention is not limited to a particular one. From the viewpoint of water absorbent property, easiness in controlling polymerization, and the like, the polymerization method is preferably spray drop polymerization in which a monomer aqueous solution is dispersed in a gaseous phase or aqueous solution polymerization in which a monomer aqueous solution is directly polymerized, more preferably the aqueous solution polymerization. Among various aqueous solution polymerizations, continuous aqueous solution polymerization is particularly preferable, which may be any of continuous belt polymerization and continuous kneader polymerization. Note that polymerization, which is carried out while a monomer is dispersed at a concentration higher than a saturating concentration of a monomer aqueous solution, may be called slurry polymerization. Such slurry (aqueous dispersion) polymerization is encompassed in the aqueous solution polymerization of the present invention.

Concrete examples of continuous belt polymerization are disclosed in U.S. Pat. No. 4,893,999, U.S. Pat. No. 6,241,928, US Patent Application Publication No. 2005/215734, and the like, and concrete examples of continuous kneader polymerization are disclosed in U.S. Pat. No. 6,987,151, U.S. Pat. No. 6,710,141, and the like. By employing any of these continuous aqueous solution polymerizations, efficiency in manufacturing the water-absorbing resin is improved.

Examples of the continuous aqueous solution polymerization, in particular, preferable examples of the foaming polymerization encompass high-temperature initiating polymerization and high concentration polymerization. The "high-temperature initiating polymerization" is a polymerization method in which polymerization is started when a temperature of the monomer aqueous solution is preferably 30° C. or higher, more preferably 35° C. or higher, still more preferably 40° C. or higher, particularly preferably 50° C. or higher (and an upper limit is a boiling point). The "high concentration polymerization" is a polymerization method in which polymerization is carried out with a monomer concentration of preferably 30 wt % or higher, more preferably 35 wt % or higher, still more preferably 40 wt % or higher, particularly preferably 45 wt % or higher (and an upper limit is a saturating concentration). These polymerization methods can be used in combination. Further, the polymerization is preferably carried out at the above described polymerization temperature (highest achieving temperature).

These polymerization methods can be carried out in an air atmosphere. From the viewpoint of color tone, the polymerization methods are preferably carried out in an atmosphere of inert gas such as nitrogen or argon. In this case, for example, it is preferable to control an oxygen concentration to 1 volume % or lower.

It is possible to employ foaming polymerization which is carried out by dispersing gas bubbles (such as of the inert gas; particularly preferably gas bubbles having a diameter of 1 nm to 1 mm) in a monomer aqueous solution. Note that it is preferable that dissolved oxygen in the monomer or the monomer aqueous solution is sufficiently substituted by inert gas (so that the dissolved oxygen exists by, for example, less than 1 (mg/l)).

(2-4) Gel-Crushing Step

In this step, the hydrogel obtained in the polymerization step is gel-crushed with the use of, for example, a gel-crusher such as a kneader, a meat chopper, or a cutter mill so that particles of hydrogel (hereinafter, referred to as "particulate hydrogel") are obtained. Note that, in a case where the polymerization step is carried out by the kneader polymerization, the polymerization step and the gel-crushing step are simultaneously carried out.

Note that, in this specification, the "particulate hydrogel" is also encompassed in the "water-containing gel-like cross-linked polymer".

The gel-crushing step of the present invention is not limited to a particular one, and a gel-crushing method disclosed in International Publication No. 2011/126079 can be preferably employed. According to the gel-crushing method, a hydrogel containing 10 wt % to 80 wt % of a resin solid content is gel-crushed with gel grinding energy (GGE) of 18 to 60 (J/g) or gel grinding energy (2) (GGE(2)) of 9 to 40 (J/g).

Note that, from the viewpoint of easiness in removal of acetic acid, water absorbent property, and color tone, a temperature at which the hydrogel is gel-crushed (i.e., from when polymerization ends to when drying starts) is controlled (i.e., kept or raised) to be in a range of preferably 40° C. to 95° C., more preferably 50° C. to 80° C., still more preferably 60° C. to 70° C.

In the gel-crushing step, from the viewpoint of easiness in removal of acetic acid, water absorbent property, and color tone, it is possible to add water, polyhydric alcohol, a mixed solution of water and polyhydric alcohol, an aqueous solution of polyvalent metal (salt), vapor thereof, or the like. Further, fine powder of water-absorbing resin, various additives, and the like can be added and kneaded.

The resin solid content in the particulate hydrogel obtained by the gel-crushing step is in a range of preferably 10 wt % to 70 wt %, more preferably 15 wt % to 65 wt %, still more preferably 30 wt % to 55 wt %, from the viewpoint of physical property. Moreover, a weight average particle diameter (D50) of the particulate hydrogel is preferably 350 μm to 2000 μm, more preferably 400 μm to 1500 μm, still more preferably 500 μm to 1000 μm. Moreover, a logarithmic standard deviation (σζ) of particle size distribution of the particulate hydrogel is preferably 0.2 to 1.5, more preferably 0.2 to 1.2, still more preferably 0.2 to 1.0.

In a case where the weight average particle diameter (D50) is larger than 2000 μm, shearing force or compressive force exerted on the particulate hydrogel may be uneven and/or insufficient.

Moreover, it becomes difficult to remove acetic acid in the drying step due to decrease in specific surface area. Further, the physical property of the particulate hydrogel becomes uneven because particles, which have different physical properties, are generated in the pulverization step due to unevenness in drying (i.e., difference in degree of drying between inside and surface part of the particulate hydrogel). As a result, the physical property of the entire water-absorbing resin may be deteriorated.

In a case where the foaming polymerization is carried out, it sometimes happens that gas bubbles in the water-containing gel-like cross-linked polymer remain in the particulate hydrogel and therefore an intended average sphericity or internal gas bubbles ratio (later described) cannot be obtained. In a case where the weight average particle diameter (D50) is smaller than 350 μm, a surface area of the particulate hydrogel becomes large and therefore the particulate hydrogel is extremely easily dried. This causes insufficient reduction in acetic acid and the residual monomer in the drying step. That is, acetic acid and/or the residual monomer are insufficiently reduced. As a result, an amount of acetic acid and a monomer which remain in the product may be increased.

(2-5) Drying Step

In this step, the particulate hydrogel obtained in the polymerization step and/or the gel-crushing step is dried to obtain a dried polymer that has an intended resin solid content. The resin solid content is calculated from a drying loss (i.e., a change in weight when 1 g of the particulate hydrogel is heated at 180° C. for 3 hours), and is preferably 80 wt % or higher, more preferably in a range of 85 wt % to 99 wt %, still more preferably in a range of 90 wt % to 98 wt %, particularly preferably in a range of 92 wt % to 97 wt %.

(Removal of Acetic Acid)

According to the present invention, the drying method is not limited to a particular one, and a known drying method can be employed. Examples of such a drying method encompass drying by heating such as hot air drying, drying under reduced pressure, infrared drying, microwave drying, high humidity drying using high temperature steam, drying with a drum dryer, and drying with a paddle dryer. Among these, the drying by heating, the hot air drying, the high humidity drying using high temperature steam are more preferable. Examples of the heating method in the drying step encompass hot air heat transfer, radiant heat transfer (e.g., infrared rays), conductive heat transfer (e.g., heated wall surface), dielectric heating (e.g., microwaves), and the like. Among these various drying methods, the hot air drying (later described) is particularly preferable.

The "hot air drying" means a method of drying a particulate hydrogel by blowing, at a wind velocity of 0.1 (m/s) or higher, a gas (hereinafter, referred to as "hot air") at a temperature of preferably 50° C. or higher, more preferably 70° C. or higher, still more preferably 100° C. or higher. Examples of the hot air drying encompass drying with the use of a band dryer, drying with the use of a fluidized bed dryer, and the like. Preferable conditions for hot air drying (i.e., drying conditions such as a drying temperature, a wind velocity and dew point) will be described later in "Other preferable drying conditions" below.

In each of the above described ways of drying, any of the following drying methods (i.e., first method through fifth method described below) is carried out so that acetic acid contained in the water-containing gel-like cross-linked polymer is at least partially removed in the drying step. In the drying step, the acetic acid removing rate (defined in Formula 2 above) is preferably 10% or higher, more preferably 15% or higher, particularly preferably 20% or higher. An upper limit of the removing rate is not limited to a particular one and, from the viewpoint of productivity, the upper limit is preferably 70% or lower, more preferably 50% or lower.

Note that the present invention does not encompass drying by azeotropic dehydration, because a solvent odor of a hydrophobic organic solvent (e.g., n-heptane or cyclohexane) which is used in the azeotropic dehydration may remain in a polyacrylic acid (salt)-based water-absorbing resin. Here, the "drying by azeotropic dehydration" indicates a process of drying a water-containing gel-like cross-linked polymer by carrying out dehydration by azeotropic distillation. Note that a hydrophobic solvent is generally used in the azeotropic dehydration, and therefore the azeotropic dehydration is carried out at a relatively low temperature (i.e., 100° C. or lower). On this account, the present invention employs any of the drying methods described below in order to carry out the drying at a drying temperature (e.g., in a range of 150° C. to 250° C.) which is suitable for removing acetic acid in the present invention.

According to the present invention, acetic acid is removed in the drying step by carrying out any one of the following methods (i.e., first method through fifth method), preferably by simultaneously carrying out any two of the following methods, more preferably by simultaneously carrying out any three of the following methods, still more preferably by simultaneously carrying out any four of the following methods, particularly preferably by simultaneously carrying out the following five methods. Further, it is more preferable to carry out any of the following methods in addition to the methods for removing acetic acid carried out in the polymerization step.

(First Method)

According to the present invention, acetic acid is removed with a first method in the drying step. In the first method, a particulate hydrogel supplied in the drying step is controlled to have a weight average particle diameter (D50) of 350 μm to 2000 μm and a logarithmic standard deviation (σζ) of particle size distribution of 0.2 to 1.5. By drying the particulate hydrogel having the particle size, acetic acid contained in the particulate hydrogel is at least partially removed.

It is still more preferable to control the particle size of the particulate hydrogel to the range described in (2-4) above so as to increase or optimize the specific surface area. This makes it possible to efficiently carry out removal of acetic acid in the drying.

(Second Method)

According to the present invention, acetic acid is removed with a second method in the drying step. In the second method, hot air drying is carried out on a particulate hydrogel, in which a concentration of solid content is 50 wt % or lower, so that contained acetic acid is at least partially removed. That is, acetic acid contained in the particulate hydrogel is at least partially removed. By thus drying the particulate hydrogel which has the lower concentration of solid content, acetic acid is easily volatilized, and this makes it possible to efficiently remove acetic acid. Note that the concentration of solid content is preferably in a range of 25 wt % to 45 wt %.

(Third Method)

According to the present invention, acetic acid is removed with a third method in the drying step. In the third method, particulate hydrogel, to which a drying aid has been added, is dried so that contained acetic acid is at least partially removed. That is, acetic acid contained in the particulate hydrogel is at least partially removed. By adding the drying aid, gaps between gel particles are widely secured in the drying, and it is therefore possible to efficiently remove acetic acid.

The drying aid is preferably water-insoluble fine particles, more preferably inorganic fine particles or water-absorbing resin fine particles. These drying aids are added to the hydrogel in the polymerization step or the gel-crushing step. The drying aids are preferably mixed with the hydrogel, still more preferably covers the hydrogel. A used amount of the drying aid is preferably 30 wt % or lower, more preferably in a range of 0.1 wt % to 25 wt %, still more preferably in a range of 1 wt % to 20 wt %, relative to a solid content of the hydrogel.

Further, instead of the inorganic fine particles or the water-absorbing resin fine particles, a gel fluidizer, a flocculant, or a flocculation inhibitor can be used as the drying aid. These compounds are disclosed in, for example, Japanese Patent Application Publication Tokukai No. 2006-160774, Japanese Patent Application Publication Tokukai No. 2001-213914, and Japanese Patent Application Publication Tokukai No. 2007-071415.

Specifically, examples of these compounds encompass long chain fatty ester, long chain fatty acid and salt thereof, long chain aliphatic alcohol, long chain aliphatic amid, and the like. Each of these compounds is used within the above described range (i.e., the used amount of drying aid), and is suitable for removing acetic acid in the drying step.

(Fourth and Fifth Methods)

According to the present invention, acetic acid is removed with a fourth method and/or a fifth method in the drying step. In the fourth method, the particulate hydrogel is dried for 5 minutes or more at a drying temperature in a range of 165° C. to 230° C. in the drying step. In the fifth method, an ambient dewing point is controlled to be in a range of 50° C. to 100° C. or a pressure is reduced by 0.1% to 5% from the atmospheric pressure, during 50% or more of drying time in the drying step.

The "ambient dewing point" indicates a dewing point of air that exists in an atmosphere in which the drying step is carried out. The ambient dewing point can be controlled to be in a range of 50° C. to 100° C. by, for example, blowing steam in or controlling a circulation ratio of hot air.

By the drying method, contained acetic acid is at least partially removed. That is, acetic acid contained in the particulate hydrogel is at least partially removed. By controlling the drying temperature, the dewing point, and the drying time to fall within the above described range, it is possible to efficiently remove acetic acid. Note that more preferable drying conditions are described below.

(Other Preferable Drying Conditions)

The drying step of the present invention is not limited to a particular drying method, and any of various drying methods can be employed. Examples of the drying method encompass drying by heating, typically, hot air drying, drying under reduced pressure, drying with a fluidized bed, infrared drying, microwave drying, drying with a drum dryer, and high humidity drying using high temperature steam. Among these, from the viewpoint of easiness in removal of acetic acid and water-absorbing property, it is particularly preferable to carry out hot air drying with the use of a gas whose dewing point is in a range of preferably 40° C. to 100° C., more preferably 50° C. to 90° C., and it is still more preferable to carry out hot air drying at the following temperature range.

That is, from the viewpoint of easiness in removal of acetic acid, water absorbent property, and color tone, the drying temperature is controlled (i.e., heated up) to preferably a temperature equal to or higher than the boiling point (i.e., 118° C.) of acetic acid, more preferably be in a range of 150° C. to 250° C., still more preferably 165° C. to 230° C. Note that, in a case of the drying by heating or the high humidity drying, a temperature of a heating medium is assumed as the drying temperature. Moreover, in a case of the hot air drying, hot air is the heating medium, and accordingly a temperature of the hot air is assumed as the drying temperature. In a case of the infrared drying or the microwave drying, a surface temperature of the particulate hydrogel is assumed as the drying temperature. The drying time is most preferably 20 minutes to 60 minutes.

Here, a preferable dewing point in the drying falls within the above described range, and the hot air drying is carried out at the temperature and the dewing point. Note that, in the present invention, a preferable dryer is (i) a ventilating band dryer or a fluidized bed dryer which uses hot air or (ii) a rotationally stirring heating dryer (e.g., rotating drum dryer) which includes a rotationally stirring blade or a rotationally stirring container and in which a wall surface is heated (if needed, by supplying hot air).

By thus controlling the drying temperature and the drying time to fall within the above described ranges, it is possible to sufficiently remove acetic acid from the particulate hydrogel, and it is further possible to obtain the water-absorbing resin whose water absorption capacity (CRC), water soluble component (Ext), and color tone fall within intended ranges (see [3] below).

In a case where the hot air drying is carried out, it is preferable to supply hot air in a perpendicular (i.e., vertical) direction relative to the hydrogel at a wind velocity of preferably 0.8 to 2.5 (m/s), more preferably 1.0 to 2.0 (m/s), in order to further attain the object of the present invention.

By thus controlling the wind velocity of the hot air to fall within the above described range, it is possible to control a moisture content of a resultant dried polymer to fall within an intended range, and it is further possible to improve water absorbing speed.

According to the present invention, it is preferable to cause exhaust gas, which has been generated when acetic acid is removed and contains acetic acid, to make contact with an alkaline liquid so that acetic acid is absorbed by the alkaline liquid. Note that the alkaline liquid is an aqueous solution of a compound such as alkali metal hydroxide or alkali metal carbonate. Specifically, the alkaline liquid is in a range of a 0.01 wt % to 50 wt % of alkali aqueous solution and is, in particular, a sodium hydroxide aqueous solution. The process of making the exhaust gas to make contact with the alkaline liquid can be carried out with the use of, for example, a scrubber (i.e., exhaust gas scrubbing device). This process can be carried out in all the steps in which acetic acid is removed. Note, however, that it is particularly useful to carry out this process in the drying step. In the drying step, the residual monomer is sufficiently reduced, and accordingly merely a small amount of acrylic acid is to be evaporated. Therefore, in the drying step, acrylic acid is reused arbitrarily. The liquid obtained from the alkaline liquid, which has absorbed acetic acid, is preferably discarded.

(2-6) Pulverization Step, Classification Step

In this step, water-absorbing resin powder (for convenience, a water-absorbing resin before being subjected to surface crosslinking is referred to as "water-absorbing resin powder") is obtained by pulverizing a dried polymer (i.e., pulverization step) obtained in the drying step so that the particle size is adjusted to a predetermined range (i.e., classification step).

Note that, for example, in a case where the hydrogel obtained in the polymerization step is in a particulate form, the pulverization step may not be carried out after the drying step. In such a case, water-absorbing resin powder is to be obtained by the drying step. As such, in this specification, "water-absorbing resin powder obtained after the drying step" encompasses both (i) water-absorbing resin powder obtained by the drying step and (ii) water-absorbing resin powder obtained as a result of subjecting a dried polymer, which has been obtained by the drying step, to the pulverization step and/or the classification step.

An apparatus which is used in the pulverization step of the present invention is not limited to a particular one. Examples of such an apparatus encompass a high-speed rotating pulverizer (such as a roll mill, a hammer mill, a screw mill, or a pin mill), a vibrating mill, a roll granulator, a knuckle type pulverizer, a cylindrical mixer, and the like, and one or more of these are used.

Among these, the roll mill is preferable. In order to control the particle diameter, the particle size distribution, and the average sphericity as described later, it is preferable to use a multiple-stage roll mill. This makes it possible to easily attain a sharp particle size distribution. That is, in the pulverization step which is carried out after the drying step, it is preferable to use the multiple-stage roll mill.

The number of stages provided in the multiple-stage roll mill is preferably 2 or more, more preferably 3 or more. Note that an upper limit of the number of stages is not limited to a particular one, and is preferably approximately 10. It is still more preferable to combine the pulverization step with the classification step (later described) such that particles, which have a particle diameter larger than an intended particle diameter (i.e., particles remained on a sieve whose mesh size is preferably 300 μm to 2000 μm, more preferably 600 μm to 1200 μm, for example 850 μm) are returned to the pulverization step.

A method for adjusting the particle size in the classifying step of the present invention is not limited to a particular one. For example, it is possible to employ sieve classification which is carried out with the use of a JIS standard sieve (JIS Z8801-1 (2000)). Note that the adjustment of the particle size of the water-absorbing resin is not carried out only in the pulverization step and the classification step but can also be carried out as appropriate in the polymerization step (in particular, spray drop polymerization) and the other steps (e.g., granulating step and fine powder collecting step).

In the present invention, the weight average particle diameter (D50) of the water-absorbing resin powder (i.e., polyacrylic acid (salt)-based water-absorbing resin) is 300 μm to 600 μm, preferably 350 μm to 600 μm, more preferably 400 μm to 600 μm, still more preferably 400 μm to 500 μm.

A ratio of particles, which are contained in the water-absorbing resin powder and has a particle diameter smaller than 150 μm, is in a range of preferably 0 wt % to wt %, more preferably 0 wt % to 5 wt %, still more preferably 0 wt % to 1 wt %. In the water-absorbing resin powder, a ratio of particles having a particle diameter of 850 μm or larger is in a range of preferably 0 wt % to 5 wt %, more preferably 0 wt % to 3 wt %, still more preferably 0 wt % to 1 wt %.

Further, a logarithmic standard deviation ($\sigma\zeta$) of particle size distribution of the water-absorbing resin powder is preferably 0.20 to 0.50, more preferably 0.25 to 0.40, still more preferably 0.27 to 0.35.

Note that the particle size of the water-absorbing resin powder is measured with the use of a standard sieve in accordance with measuring methods disclosed in International Publication No. 2004/69915 and EDANA ERT420.2-02.

Note that types of standard sieve can be added as appropriate and, in the present invention, standard sieves having respective mesh sizes of 850 μm, 710 μm, 600 μm, 500 μm, 425 μm, 300 μm, 212 μm, 150 μm, and 45 μm are used.

Moreover, the weight average particle diameter (D50) and the logarithmic standard deviation ($\sigma\zeta$) of particle diameter distribution are measured with the method described in the specification of U.S. Pat. No. 7,638,570, columns 27 and 28, "(3) Mass-Average Particle Diameter (D50) and Logarithmic Standard Deviation ($\sigma\zeta$) of Particle Diameter Distribution".

The particle size (i.e., the weight average particle diameter (D50), the logarithmic standard deviation ($\sigma\zeta$) of particle diameter distribution, the ratio of particles having particle diameter of smaller than 150 μm, and the ratio of particles having particle diameter of 850 μm or larger) of the water-absorbing resin powder is also applied to (i) a water-absorbing resin after surface crosslinking (i.e., a surface cross-linked water-absorbing resin; hereinafter, for convenience, sometimes referred to as "water-absorbing resin particles") and (ii) water-absorbing resin as an end product (i.e., the polyacrylic acid (salt)-based water-absorbing resin). Therefore, it is preferable to carry out surface crosslinking on the water-absorbing resin powder so that the above described particle size range is maintained.

(2-7) Surface Crosslinking Step

In a surface crosslinking step, a part having a higher crosslinking density is provided on a surface layer (i.e., a part within several tens of micrometers from the surface) of the water-absorbing resin powder which has been obtained through the above described steps. The surface crosslinking step includes (i) a step of obtaining a mixture by mixing the water-absorbing resin powder with a surface crosslinking agent solution, (ii) a step of heating the mixture, and, if needed, (iii) a step of cooling the mixture which has been heated.

In the surface crosslinking step, a water-absorbing resin (i.e., water-absorbing resin particles), which has been surface cross-linked, is obtained through radical crosslinking, surface polymerization, crosslinking reaction with the surface crosslinking agent, and the like on the surface of the water-absorbing resin powder.

(Removal of Acetic Acid)

In the surface crosslinking step of the present invention, acetic acid is at least partially removed by carrying out any one of four methods described below, preferably simultaneously carrying out any two of the four methods, more preferably simultaneously carrying out any three of the four methods, still more preferably simultaneously carrying out the four methods.

In the surface crosslinking step, an acetic acid removing rate (defined in Formula 2 above) is preferably 0.5% or higher, more preferably 0.7% or higher, particularly preferably 1% or higher. An upper limit of the removing rate is not limited to a particular one and is, from the viewpoint of productivity, preferably 10% or lower, more preferably 5% or lower, particularly preferably 3% or lower. As such, the acetic acid removing rate in the surface crosslinking step can be selected as appropriate within the above described range, and is in a range of preferably 0.5% to 10%, more preferably 0.7% to 5%, still more preferably 1% to 3%.

It is still more preferable to carry out any of the following methods in addition to the methods for removing acetic acid carried out in the polymerization step and/or the drying step. Note that acetic acid is hardly diffused which exists in the dried water-absorbing resin powder. However, acetic acid, which exists in the vicinity of the surface of the water-absorbing resin powder, is removed. Therefore, even though the acetic acid removing rate is low in the surface crosslinking step, an odor reduction effect is sometimes greatly brought about (in a case where, in particular, the odor is smelled without swelling the water-absorbing resin powder).

(First Method)

According to the present invention, acetic acid is removed with a first method in the surface crosslinking step. In the first method, surface crosslinking is carried out in the presence of an acidic compound so that contained acetic acid is at least partially removed. That is, in the first method, surface crosslinking of the water-absorbing resin powder is carried out in the presence of acidic compound, and acetic acid contained in the water-absorbing resin powder is at least partially removed by the first method.

As above described, acetic acid salt is nonvolatile. Therefore, when the surface of water-absorbing resin is acidified with the use of the acidic compound, salt exchange occurs by which acetic acid salt, which exists on the surface of the water-absorbing resin, is turned into acetic acid. By carrying out a heat treatment as described below in this state, it is possible to efficiently remove acetic acid.

Note that the removal of acetic acid is facilitated due to the presence of water in the heat treatment, and it is therefore preferable to carry out the heat treatment in the presence of a predetermined amount of water, in particular in the presence of water whose amount falls within the above described range.

The acidic compound is preferably organic acid or inorganic acid, more preferably nonpolymeric organic acid or nonpolymeric inorganic acid. Specifically, examples of the acidic compound encompass inorganic acid such as aluminum sulfate and phosphoric acid, and organic acid such as lactic acid, citric acid, and oxalic acid. A used amount of the acidic compound is in a range of preferably 0 part by weight to 10 parts by weight, more preferably 0.01 part by weight to 5 parts by weight, still more preferably 0.05 part by weight to 1 part by weight, relative to 100 parts by weight of the water-absorbing resin, i.e., 100 parts by weight of the water-absorbing resin powder.

(Second Method)

According to the present invention, acetic acid is removed with a second method in the surface crosslinking step. In the second method, water-absorbing resin powder, to which a surface crosslinking agent has been added, is heated at a heating temperature in a range of 165° C. to 230° C. for 5 minutes or longer so that contained acetic acid is at least partially removed.

After the water-absorbing resin powder is remoistened by adding the surface crosslinking agent solution (i.e., a moisture content is increased by adding water), it is possible to efficiently remove acetic acid by heating the water-absorbing resin powder at 165° C. or higher (preferably at a temperature in a range of 165° C. to 230° C.). Further, an excessive volatile surface crosslinking agent can be removed, and it is therefore possible to preferably reduce odor derived from the surface crosslinking agent. Note that, in a case where the remoistening is not carried out or in a case where the heating temperature is low even though remoistening is carried out, acetic acid cannot be sufficiently removed. The "surface crosslinking agent solution" will be described later.

(Third Method)

According to the present invention, acetic acid is removed with a third method in the surface crosslinking step. In the third method, after a surface crosslinking agent is added, steam is caused to exist 50% or more of the heat treatment time so that contained acetic acid is at least partially removed. That is, by causing the steam to exist, in particular by introducing the steam into a heat treatment device (i.e., a reacting device), acetic acid contained in the water-absorbing resin powder is at least partially removed.

After the water-absorbing resin powder is remoistened by adding a surface crosslinking agent solution (i.e., a moisture content is increased by adding water), it is possible to efficiently remove acetic acid by heating the water-absorbing resin powder at a particularly high dewing point in the presence of steam. Note that the dewing point is in a range of preferably 0° C. to 100° C., still more preferably 5° C. to 100° C. Note that the heating temperature is preferably in a range of 100° C. to 230° C., and the heating time is preferably 5 minutes or more.

(Fourth Method)

According to the present invention, acetic acid is removed with a fourth method in the surface crosslinking step. In the fourth method, after the surface crosslinking agent is added to the water-absorbing resin powder, a pressure is reduced by 0.1% to 5% with respect to the atmospheric pressure during 50% or more of the heat treatment time so that contained acetic acid is at least partially removed. That is, acetic acid contained in the water-absorbing resin powder is at least partially removed. By thus slightly reducing the pressure after remoistening is carried out by adding the surface crosslinking agent solution (i.e., a moisture content is increased by adding water), it is possible to efficiently remove acetic acid. Note that the degree of reducing pressure is in a range of preferably 0.5% to 5%, still more preferably 1% to 3%.

(Surface Crosslinking Agent)

The surface crosslinking agent that can be used in the present invention is not limited to a particular one. Examples of the surface crosslinking agent encompass various kinds of organic surface crosslinking agents and inorganic surface crosslinking agents. Among these, a surface crosslinking agent which can react with a carboxyl group is preferable, from the viewpoint of physical properties of the water-absorbing resin and ease of handling the surface crosslinking agent.

More specifically, examples of the surface crosslinking agent encompass polyhydric alcohol compounds such as mono, di, tri, tetra, or polyethyleneglycol, monopropyleneglycol, 1,3-propanediol, dipropyleneglycol, 2,3,4-trimethyl-1,3-pentandiol, polypropyleneglycol, glycerin, polyglycerin, 2-butene-1,4-diol, 1,4-butandiol, 1,3-butandiol, 1,5-pentandiol, 1,6-hexanediol, and 1,2-cyclohexanedimethanol; epoxy compounds such as ethyleneglycol diglycidyl ether and glycidol; polyhydric amine compounds such as ethylenediamine, diethylenetriamine, triethylenetetramine, tetraethylenepentamine, pentaethylenehexamine, polyethyleneimine, and polyamidepolyamine; haloepoxy compounds such as epichlorohydrin, epibromhydrin, and α-methyl epichlorohydrin; a condensate of the polyhydric amine compound and the haloepoxy compound; an oxazoline compound; a monovalent or polyvalent oxazolidinone compound such as 2-oxazolidinone; an alkylenecarbonate compound such as ethylenecarbonate; an oxetane compound; a cyclic urea compound such as 2-imidazolidinone; and the like.

Among these, the oxazolidinone compound, the alkylenecarbonate compound, or the polyhydric alcohol compound is preferable, and it is more preferable to use in combination with the alkylenecarbonate compound and the polyhydric alcohol compound.

An amount of the surface crosslinking agent used in the present invention (or, in a case where a plurality of surface crosslinking agents are used, a total amount of the plurality of surface crosslinking agents) varies depending on the used surface crosslinking agent(s), a combination of used surface crosslinking agents and the like, and is in a range of preferably 0.001 part by weight to 10 parts by weight, more preferably 0.01 part by weight to 5 parts by weight, relative to 100 parts by weight of the water-absorbing resin powder which is subjected to the surface crosslinking step.

(Solvent)

According to the embodiment of the present invention, it is preferable to add and mix the water-absorbing resin powder with a surface crosslinking agent solution which is obtained by dissolving the surface crosslinking agent in water. In this case, a used amount of water varies depending on a moisture content of the water-absorbing resin powder, and is in a range of preferably 0.5 part by weight to 20 parts by weight, more preferably 0.5 part by weight to 10 parts by weight, relative to 100 parts by weight of the water-absorbing resin powder.

Alternatively, it is possible to use a hydrophilic organic solvent instead of water. In this case, a used amount of the hydrophilic organic solvent is in a range of preferably 0 part by weight to 10 parts by weight, more preferably 0 part by weight to 5 parts by weight, relative to 100 parts by weight of the water-absorbing resin powder.

Alternatively, water-insoluble fine particles and a surfactant can be contained to an extent that the effects of the present invention would not be inhibited. In this case, a used amount of such compounds is in a range of preferably 0 part by weight to 10 parts by weight, more preferably 0 part by weight to 5 parts by weight, still more preferably 0 part by weight to 1 part by weight, relative to 100 parts by weight of the water-absorbing resin powder. Note that contents disclosed in U.S. Pat. No. 7,473,739 are preferably applied.

(Mixing Step)

According to the present invention, a method of adding and mixing the surface crosslinking agent solution in the surface crosslinking step is not limited to a particular one. According to the present invention, water as a solvent, a hydrophilic organic solvent, or a mixture of these is prepared in advance, and the prepared solvent is then added to and mixed with the water-absorbing resin powder preferably by being sprayed or dropped onto the water-absorbing resin powder, more preferably by being sprayed onto the water-absorbing resin powder.

A mixer, which is used to mix the surface crosslinking agent solution with the water-absorbing resin powder, is not limited to a particular one, and is preferably a high-speed stirring mixer, more preferably a high-speed stirring continuous mixer. More specifically, the mixer can be, for example, Turbulizer (manufactured by Hosokawa Micron Corporation), Loedige mixer (manufactured by Loedige) or the like.

(Heat Treatment Step)

The water-absorbing resin powder, which has been added and mixed with the surface crosslinking agent solution, is subjected to heat treatment, and then is subjected to cool treatment if needed.

The heat treatment is carried out at a temperature in a range of preferably 70° C. to 300° C., more preferably 120° C. to 250° C., still more preferably 150° C. to 250° C. Note that the temperature indicates a temperature of the mixture of the water-absorbing resin powder and the surface crosslinking agent, and is also referred to as "heating temperature".

In a case where the heating temperature is lower than 70° C., surface crosslinking of the water-absorbing resin powder is insufficiently carried out, and therefore water absorption capacity under load (AAP) and saline flow conductivity (SFC) are decreased. On the other hand, in a case where the heating temperature is higher than 300° C., the water-absorbing resin is unfavorably colored.

Moreover, a time of heat treatment (i.e., heating time) is in a range of preferably 1 minute to 2 hours, more preferably 5 minutes to 1.5 hours. Note that the heat treatment can be carried out with the use of a general dryer or a general heating oven.

(2-8) Remoistening Step

In the remoistening step, at least one additive, which is selected from the group consisting of a polyvalent metal salt compound, a polycationic polymer, a chelating agent, an inorganic reducing agent, and a hydroxycarboxylic compound (which are described later), is added to the water-absorbing resin particles obtained in the surface crosslinking step. Moreover, adding of water to the water-absorbing resin particles is also included in the remoistening step.

The additive is preferably added in a form of aqueous solution or slurry. In this case, the water-absorbing resin thus swells water again, and therefore this step is referred to as "remoistening step". Note that the additive can be added and mixed concurrently with the surface crosslinking agent solution described above. A moisture content of the water-absorbing resin particles (i.e., the surface cross-linked water-absorbing resin obtained in the surface crosslinking step) is preferably the later described moisture content, particularly controlled to a moisture content in a range of 2 wt % to 9 wt %.

(Removal of Acetic Acid)

In the remoistening step of the present invention, acetic acid is at least partially removed by carrying out any one of three methods described below, preferably simultaneously carrying out any two of the three methods, more preferably simultaneously carrying out the three methods.

In the remoistening step, an acetic acid removing rate (defined in Formula 2 above) is preferably 0.5% or higher, more preferably 1% or higher, particularly preferably 2% or higher. An upper limit of the removing rate is not limited to a particular one and is, from the viewpoint of productivity, preferably 10% or lower, more preferably 5% or lower.

It is still more preferable to carry out any of the following methods in addition to the methods for removing acetic acid carried out in the polymerization step, the drying step, and/or the surface crosslinking step. Note that acetic acid is hardly diffused which exists in the dried water-absorbing resin.

However, acetic acid, which exists in the vicinity of the surface of the water-absorbing resin, is removed. Therefore, even though the acetic acid removing rate is low in the remoistening step, an odor reduction effect is sometimes greatly brought about (in a case where, in particular, the odor is smelled without swelling the water-absorbing resin).

(First Method)

According to the present invention, acetic acid is removed with a first method in the remoistening step. In the first method, 0.5 part by weight to 15 parts by weight of water is added to 100 parts by weight of the water-absorbing resin obtained by the surface crosslinking, and the mixture is then subjected to heat treatment. By this first method, contained acetic acid is at least partially removed. By thus carrying out the heat treatment after the remoistening is carried out by adding water (i.e., a moisture content is increased by adding water), it is possible to efficiently remove acetic acid.

That is, by carrying out the heat treatment after the surface cross-linked water-absorbing resin is remoistened by adding water (i.e., a moisture content is increased by adding water), it is possible to efficiently remove acetic acid.

Note that, in a case where the remoistening is not carried out or in a case where the heating temperature is low even though remoistening is carried out, acetic acid cannot be sufficiently removed. An amount of water is in a range of preferably 1 part by weight to 13 parts by weight, more preferably 3 parts by weight to 10 parts by weight, relative to 100 parts by weight of the water-absorbing resin particles. The heating temperature is preferably in a range of 30° C. to 99° C., more preferably a heating temperature described later in (Third method).

(Second Method)

The second method of removing acetic acid (i.e., improving an acetic acid removing rate) in the remoistening step of the present invention is a method in which polyvalent metal ions are added in the remoistening step. That is, in the second method, polyvalent metal ions are added to the water-absorbing resin, which has been obtained by the surface crosslinking, so that contained acetic acid is at least partially removed or insolubilized.

Note that the "polyvalent metal ions are added to the water-absorbing resin, which has been obtained by the surface crosslinking" encompasses that (i) polyvalent metal ions are added to the water-absorbing resin as an aqueous solution and (ii) polyvalent metal salt is added to a water-absorbing resin which has been obtained by adding 0.5 part by weight to 15 parts by weight of water to 100 parts by weight of the water-absorbing resin.

By carrying out heat treatment after the water-absorbing resin is remoistened by the addition of the aqueous solution of polyvalent metal ions (i.e., a moisture content is increased by adding water), it is possible to efficiently remove acetic acid. This allows improvement in mixing property of the water-absorbing resin with water, and it is therefore possible to more efficiently remove acetic acid.

(Third Method)

According to the present invention, acetic acid is removed with a third method in the remoistening step. In the third method, a temperature of the water-absorbing resin, which has been remoistened, is maintained within a range of 65° C. to 99° C. for 5 minutes or more (and an upper limit is approximately 2 hours) so that contained acetic acid is at least partially removed. By heating, acetic acid is more easily evaporated, and it is therefore possible to more efficiently remove acetic acid. In a case where the polyvalent metal ions are used, the mixing property of the water-absorbing resin with water is further improved, and it is therefore possible to more efficiently remove acetic acid.

Note that the "water-absorbing resin, which has been remoistened" encompasses (i) a water-absorbing resin to which 0.5 part by weight to 15 parts by weight of water has been added to 100 parts by weight of the water-absorbing resin that has been obtained by surface crosslinking, (ii) a water-absorbing resin obtained by adding polyvalent metal salt to the water-absorbing resin of the above (i), and (iii) a water-absorbing resin obtained by adding an aqueous solution of polyvalent metal ions to a surface cross-linked water-absorbing resin.

(Polyvalent Metal Salt Compound)

Examples of the polyvalent metal salt compound which can be used in the present invention encompass varies inorganic polyvalent metal salt compounds and varies organic polyvalent metal salt compounds. Among these, the polyvalent metal salt compound can be made up of any of elements such as aluminum, zirconium, iron, titanium, calcium, magnesium, and zinc. The polyvalent metal salt compound serves as a source of polyvalent metal ions.

The polyvalent metal salt compound preferably is water-soluble, more preferably has water solubility of 2 wt % or higher relative to 25° C. water, still more preferably has water solubility of 5 wt % or higher relative to 25° C. water.

Specifically, examples of the polyvalent metal salt compound having such water solubility encompass inorganic acid salt such as aluminum chloride, polyaluminum chloride, aluminum sulfate, aluminum nitrate, bis aluminum potassium sulfate, bis aluminum sodium sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, and zirconium nitrate, and organic acid salt such as lactic acid salt of the polyvalent metals and acetic acid salt of the polyvalent metals.

Among these, the polyvalent metal salt compound is preferably an aluminum compound, more preferably aluminum chloride, polyaluminum chloride, aluminum sulfate, aluminum nitrate, bis aluminum potassium sulfate, bis aluminum sodium sulfate, potassium alum, ammonium alum, sodium alum, sodium aluminate, still more preferably aluminum sulfate.

From the viewpoint of solubility with a liquid to be absorbed such as body fluid such as urine or blood, the polyvalent metal salt compound preferably has water of crystallization, most preferably is hydrated crystal powder such as aluminum sulfate octadecahydrate or aluminum sulfate tetradecahydrate to octadecahydrate. It is possible to use only one of the polyvalent metal salt compounds or two or more of the polyvalent metal salt compounds.

A used amount of the polyvalent metal salt compound is in a range of preferably 0 part by weight to 5 parts by weight, more preferably 0.001 part by weight to 3 parts by weight, still more preferably 0.01 part by weight to 2 parts by weight, relative to 100 parts by weight of the water-absorbing resin particles. By controlling the used amount to fall within the above described range, it is possible to inhibit decrease in water absorbency and to inhibit coloring.

(Cationic Polymer)

A cationic polymer, which can be used in the present invention, is preferably a cationic polymer having an amino group, more preferably a water-soluble cationic polymer, still more preferably a cationic polymer having water solubility of 2 wt % or higher relative to 25° C. water, further preferably a cationic polymer having water solubility of 5 wt % or higher relative to 25° C. water.

Specifically, examples of the cationic polymer having such water solubility encompass polyalkyleneimine such as polyethyleneimine, polyetherpolyamine, polyetheramine, polyvinylamine, polyalkylamine, polyallylamine, polydiallylamine, poly(N-alkylarylamine), monoarylamine-diarylamine copolymer, N-alkylarylamine-monoarylamine copolymer, monoarylamine-dialkyldiallylammonium salt copolymer, diarylamine-dialkyldiallylammonium salt copolymer, polyethylenepolyamine, polypropylenepolyamine, polyamidine, and salt of these. Further, a modified cationic polymer disclosed in International Publication No. 2009/041727 is also preferably used.

A weight-average molecular weight of the cationic polymer is preferably 5000 or more, more preferably 10 thousand or more, still more preferably 30 thousand or more. An upper limit is not limited to a particular one and is preferably 1 million or less, more preferably 500 thousand or less. By controlling the weight-average molecular weight to fall within the above described range, it is possible to inhibit viscosity of the polycationic polymer. Therefore, such a polycationic polymer is excellent in ease of handling and in mixing property. Note that the weight-average molecular weight can be calculated with a known measuring method such as GPC, viscosity measuring, or static light scattering measuring.

A used amount of the polycationic polymer is in a range of preferably 0 part by weight to 5 parts by weight, more preferably 0.001 part by weight to 3 parts by weight, still more preferably 0.01 part by weight to 2 parts by weight, relative to 100 parts by weight of the water-absorbing resin particles. By controlling the used amount to fall within the above described range, it is possible to inhibit (i) decrease in water absorbency, (ii) coloring, and (iii) odor.

(Chelating Agent)

According to the present invention, a chelating agent can be further added from the viewpoint of prevention of coloring and deterioration of the obtained water-absorbing resin.

The chelating agent is preferably a polymer or nonpolymer chelating agent, more preferably a nonpolymer chelating agent. Among these, a compound selected from the group consisting of amino polyvalent carboxylic acid, organic polyvalent phosphoric acid, and amino polyvalent phosphoric acid is preferable, and a nonpolymer compound is particularly preferable.

Further, a chelating agent disclosed in European Patent No. 940148 can also be preferably used. Note that the term "polyvalent" indicates that one (1) molecule has a plurality of functional groups, preferably 2 to 30 functional groups, more preferably 3 to 20 functional groups, still more preferably 4 to 10 functional groups.

A weight-average molecular weight of the chelating agent is preferably 100 to 5000, more preferably 200 to 1000.

A used amount of the chelating agent is in a range of preferably 0.001 part by weight to 0.1 part by weight, more preferably 0.002 part by weight to 0.05 part by weight, still more preferably 0.003 part by weight to 0.04 part by weight, particularly preferably 0.004 part by weight to 0.02 part by weight, relative to 100 parts by weight of the water-absorbing resin particles. By controlling the used amount to fall within the above described range, it is possible to inhibit deterioration in initial color tone of the water-absorbing resin and deterioration in color tone with the lapse time of the water-absorbing resin.

(Inorganic Reducing Agent)

According to the present invention, an inorganic reducing agent can be further added from the viewpoint of (i) prevention of coloring and deterioration of obtained water-absorbing resin and (ii) reduction in residual monomer in the obtained water-absorbing resin.

Examples of the inorganic reducing agent encompass an inorganic reducing agent containing a sulfur atom, an inorganic reducing agent containing a phosphorus atom, and the like. The inorganic reducing agent can be an acid type or a salt type, and is preferably the salt type, where salt is preferably monovalent to polyvalent metal salt, more preferably monovalent metal salt. Specifically, the inorganic reducing agent can be, for example, (hydrogen) sulfite. Further, an inorganic reducing agent disclosed in US Patent Application Publication No. 2006/074160 can also be preferably used.

A used amount of the inorganic reducing agent is in a range of preferably 0.01 part by weight to 1.5 parts by weight, more preferably 0.05 part by weight to 1.0 part by weight, still more preferably 0.05 part by weight to 0.5 part by weight, relative to 100 parts by weight of the water-absorbing resin particles. By controlling the used amount to fall within the above described range, it is possible to inhibit deterioration in color tone with the lapse time of the water-absorbing resin and an odor of the water-absorbing resin. In particular, it is possible to inhibit generation of an odor after the water-absorbing resin absorbs, for example, a body fluid such as urine.

($\alpha$-hydroxycarboxylic Compound)

According to the present invention, an $\alpha$-hydroxycarboxylic compound can be further added from the viewpoint of prevention of coloring of obtained water-absorbing resin. Note that the "$\alpha$-hydroxycarboxylic compound" is carboxylic acid or salt thereof that has a hydroxyl group in its molecule. Specifically, the "$\alpha$-hydroxycarboxylic compound" is hydroxycarboxylic acid having a hydroxyl group in its alpha position.

The $\alpha$-hydroxycarboxylic compound is preferably a nonpolymer $\alpha$-hydroxycarboxylic compound. From the viewpoint of ease of handling and effect of addition, a molecular weight of the $\alpha$-hydroxycarboxylic compound is in a range of preferably 40 to 2000, further preferably 60 to 1000, particularly preferably 100 to 500. Moreover, the $\alpha$-hydroxycarboxylic compound is preferably water soluble. Specifically, examples of the $\alpha$-hydroxycarboxylic compound encompass glycolic acid, tartaric acid, lactic acid (salt), citric acid (salt), malic acid (salt), isocitric acid (salt), glycerinic acid (salt), poly$\alpha$-hydroxyacrylic acid (salt), and the like. Among these, lactic acid (salt) and malic acid (salt) are preferable, lactic acid (salt) is more preferable.

From the viewpoint of cost, a used amount of the $\alpha$-hydroxycarboxylic acid is in a range of preferably 0.05 part by weight to 1.0 part by weight, more preferably 0.05 part by weight to 0.5 part by weight, still more preferably 0.1 part by weight to 0.5 part by weight, relative to 100 parts by weight of the water-absorbing resin particles. By controlling the used amount to fall within the above described range, it is possible to inhibit deterioration in color tone with the lapse time of the water-absorbing resin.

(Other Additive)

In order to give various functions to the water-absorbing resin, it is possible to add an additive in addition to the above described additives. Specifically, examples of such an additive encompass a surfactant, a compound having a phosphorus atom, an oxidizer, an organic reducing agent, water-insoluble inorganic or organic powder such as silica or metal soap, a deodorant agent, an antibacterial agent, pulp, thermoplastic fiber, and the like. Further, as the surfactant, a surfactant disclosed in International Publication No. 2005/075070 can be preferably used.

A used amount of these additives is determined as appropriate in accordance with the purpose of use and is not limited to a particular one. The used amount of the additive(s) is in a range of preferably 0 part by weight to 3 parts by weight, more preferably 0 part by weight to 1 part by weight, relative to 100 parts by weight of the water-absorbing resin particles.

(2-9) Other Steps

In addition to the above described steps, it is possible to carry out, if needed, steps such as a recycling step for recycling an evaporated monomer, a granulating step, and a fine powder removing step. Moreover, it is possible to further carry out one or more of steps such as a transporting step, a storing step, a packaging step, and a reserving step.

[3] Physical Property of Polyacrylic Acid (Salt)-Based Water-Absorbing Resin

According to the water-absorbing resin of the present invention, an acetic acid content (acetic acid concentration) is in a range of 100 ppm to 7000 ppm, a propionic acid content (propionic acid concentration) is lower than 300 ppm, a residual monomer (residual monomer concentration) is less than 500 ppm, a weight average particle diameter (D50) is in a range of 300 μm to 600 μm, a logarithmic standard deviation of particle diameter, i.e., a logarithmic standard deviation ($\sigma\zeta$) of particle size distribution is in a range of 0.20 to 0.50, and a sphericity is 0.65 or higher. According to the water-absorbing resin of the present invention, the amount of $C_2$-$C_3$ organic carboxylic acid and the particle size are controlled, and therefore the water-absorbing resin has excellent water absorbent property and hardly emits acid odor in practical use. Further, from the viewpoint of odor and physical property in practical use, in a case where the water-absorbing resin is used in hygiene product, in particular, in a disposable diaper, at least one, preferably at least two including water absorption capacity under load (AAP), more preferably at least three of the following physical properties (3-1) through (3-13) are controlled to fall within intended ranges while the above described conditions of neutralization rate and salt are satisfied.

In a case where the larger number of the physical properties fall within the following ranges, the polyacrylic acid (salt)-based water-absorbing resin of the present invention can achieve sufficient performance in a high concentration disposable diaper.

The water-absorbing resin, which is obtained with the manufacturing method in accordance with the present invention, is not limited to a particular shape, and is particularly preferably in particle form. The following description will discuss physical properties of particulate water-absorbing resin, in accordance with a preferable aspect. Note that the following physical properties are defined in conformity to the EADANA method, unless otherwise noted.

(3-1) Water Absorption Capacity without Load (CRC)

A water absorption capacity without load (CRC) of the water-absorbing resin in accordance with the present invention is preferably 5 (g/g) or higher, more preferably 15 (g/g) or higher, still more preferably 25 (g/g) or higher. An upper limit is not limited to a particular one and is preferably 70 (g/g) or lower, more preferably 50 (g/g) or lower, still more preferably 40 (g/g) or lower.

In a case where the CRC is lower than 5 (g/g), the absorbency is low and such a water-absorbing resin is not suitable for an absorbent body of hygiene product such as a disposable diaper. In a case where the CRC is more than 70 (g/g), a speed of absorbing, for example, a body fluid such as urine or blood is decreased, and such a water-absorbing resin is not suitable for a disposable diaper or the like whose water absorbing speed is high. Note that the CRC can be controlled with the use of an agent such as an internal crosslinking agent or a surface crosslinking agent.

(3-2) Water Absorption Capacity Under Load (AAP)

A water absorption capacity under load (AAP) of the water-absorbing resin in accordance with the present invention is preferably 20 (g/g) or higher, more preferably 22 (g/g) or higher, still more preferably 23 (g/g) or higher, particularly preferably 24 (g/g) or higher, most preferably (g/g) or higher. An upper limit is not limited to a particular one, and is preferably 30 (g/g) or lower.

In a case where the AAP is lower than 20 (g/g), an amount of liquid returned (hereinafter, referred to as "re-wet") when a pressure is exerted on the absorbent body becomes large, and such an absorbent body is not suitable for hygiene product such as a disposable diaper. Note that the AAP can be controlled by adjusting particle size, by the use of a surface crosslinking agent, or the like.

(3-3) Saline Flow Conductivity (SFC)

A saline flow conductivity (SFC) of the water-absorbing resin in accordance with the present invention is preferably 50 ($\times 10^{-7} \cdot s \cdot cm^3 \cdot g^{-1}$) or higher, more preferably 60 ($\times 10^{-7} \cdot s \cdot cm^3 \cdot g^{-1}$) or higher, more preferably 70 ($\times 10^{-7} \cdot s \cdot cm^3 \cdot g^{-1}$) or higher, still more preferably 80 ($\times 10^{-7} \cdot s \cdot cm^3 \cdot g^{-1}$) or higher. An upper limit is not limited to a particular one, and is preferably 3000 ($\times 10^{-7} \cdot s \cdot cm^3 \cdot g^{-1}$) or lower, more preferably 2000 ($\times 10^{-7} \cdot s \cdot cm^3 \cdot g^{-1}$) or lower.

In a case where the SFC is lower than 50 ($\times 10^{-7} \cdot s \cdot cm^3 \cdot g^{-1}$), a liquid permeability relative to, for example, a body fluid such as urine and blood is low, and therefore such a water-absorbing resin is not suitable for a disposable diaper or the like which has an absorbent body containing a large used amount of water-absorbing resin. In a case where the SFC is higher than 3000 ($\times 10^{-7} \cdot s \cdot cm^3 \cdot g^{-1}$), for example, a body fluid such as urine and blood may not be sufficiently absorbed and may leak. Therefore, such a water-absorbing resin is not suitable for a disposable diaper or the like. Note that the SFC can be controlled by adjusting particle size or by the use of, for example, a surface crosslinking agent, a polyvalent metal salt, and/or a cationic polymer.

(3-4) Moisture Content

A moisture content of the water-absorbing resin in accordance with the present invention is preferably more than 0 wt % and 15 wt % or lower, more preferably in a range of 1 wt % to 13 wt %, still more preferably in a range of 2 wt % to 10 wt %, particularly preferably in a range of 2 wt % to 9 wt %. By thus controlling the moisture content to fall within the above described range, it is possible to obtain the water-absorbing resin which is excellent in powder characteristic (e.g., fluidity, transportability, and damage resistance).

Note that the "moisture content" indicates a ratio (wt %) of water with respect to 100 wt % of a mixture of the water and the water-absorbing resin (if needed, containing other components such as an additive).

(3-5) Residual Monomer

From the viewpoint of safety, a residual monomer (residual monomer concentration) in the water-absorbing resin of the present invention is preferably in a range of 0 ppm to 500 ppm, more preferably 0 ppm to 400 ppm, still more preferably 0 ppm to 300 ppm. By controlling the residual monomer to fall within the above described range, it is possible to obtain the water-absorbing resin which is less stimulating to, for example, the skin. Further, it is possible to reduce odor derived from a residual monomer.

(3-6) Acetic Acid Content (Acetic Acid Concentration) and Propionic Acid Content (Propionic Acid Concentration)

An acetic acid content (acetic acid concentration) of the water-absorbing resin in accordance with the present invention is in a range of 100 ppm to 7000 ppm, preferably 100 ppm to 5000 ppm, 100 ppm to 2000 ppm, 150 ppm to 1500 ppm, 200 ppm to 1000 ppm, in this order, and particularly preferably 400 ppm to 1000 ppm.

By controlling the acetic acid content to fall within the above described range, it is possible to obtain the water-absorbing resin whose odor is inhibited and which is excellent in water soluble component and water-absorbing property. Further, it is possible to inhibit an ammonia odor in urine.

A propionic acid content (propionic acid concentration) of the water-absorbing resin in accordance with the present invention is preferably 500 ppm or lower, preferably 450 ppm or lower, more preferably 300 ppm or lower (and a lower limit is 0 ppm).

According to the water-absorbing resin of the present invention, a ratio between the acetic acid content (ppm) and the propionic acid content (ppm) is controlled as follows: that is, the acetic acid content is higher than the propionic acid content by preferably 3 times or more, more preferably 4 times or more, still more preferably 5 times or more, particularly preferably 6 times or more. A propionic acid odor is a peculiar unpleasant odor, and an acid dissociation constant (PKa) of acetic acid is smaller than that of propionic acid. Therefore, it is preferable that the amount of propionic acid is sufficiently smaller than that of acetic acid.

(3-7) Water Soluble Component (Ext)

A water soluble component (Ext) of the water-absorbing resin in accordance with the present invention is preferably 35 wt % or lower, more preferably 25 wt % or lower, still more preferably 15 wt % or lower. A lower limit is 0 wt % but can be 3 wt % or higher or 5 wt % or higher by taking into consideration a balance with the other physical properties (e.g., CRC).

In a case where the water soluble component is higher than 35 wt %, a gel strength is low and therefore the liquid permeability of the water-absorbing resin may be deteriorated. Further, the re-wet is increased, and therefore such a water-absorbing resin is not suitable for use in a disposable diaper or the like. Note that the water soluble component can be controlled with the use of an internal crosslinking agent or the like.

In a case where the amount of acetic acid in the raw material acrylic acid is more than 10000 ppm, a water soluble component in the obtained water-absorbing resin tends to be increased.

(3-8) Water Absorbing Speed (FSR)

According to the water-absorbing resin of the present invention, a water absorbing speed (FSR) is preferably 0.10 (g/g/s) or higher, more preferably 0.15 (g/g/s) or higher, still more preferably 0.20 (g/g/s) or higher, particularly preferably 0.25 (g/g/s) or higher. An upper limit is preferably 1.0 (g/g/s) or lower, more preferably 0.5 (g/g/s) or lower, still more preferably 0.4 (g/g/s) or lower, particularly preferably 0.35 (g/g/s) or lower, from the viewpoint of a balance with the liquid permeability and in order to reduce a surface area of the water-absorbing resin for inhibiting an acid odor.

In a case where the water absorbing speed (FSR) is lower than 0.10 (g/g/s), for example, a body fluid such as urine and blood may not be sufficiently absorbed and may leak. Therefore, such a water-absorbing resin is not suitable for a disposable diaper or the like. On the other hand, in a case where the water absorbing speed (FSR) is too high, the liquid permeability may be deteriorated. In a case where a surface area of the water-absorbing resin is excessively enlarged in order to improve the FSR, an acid odor is easily generated. Note that the FSR can be controlled, for example, by foaming polymerization or by adjusting particle size.

(3-9) Particle Size

A weight average particle diameter (D50) of the water-absorbing resin in accordance with the present invention is in a range of 300 μm to 600 μm, preferably 350 μm to 600 μm, more preferably 400 μm to 600 μm, still more preferably 400 μm to 500 μm.

A ratio of particles whose particle diameter is smaller than 150 μm is in a range of preferably 0 wt % to 10 wt %, more preferably 0 wt % to 5 wt %, still more preferably 0 wt % to 1 wt %. A ratio of particles whose particle diameter is 850 μm or larger is in a range of preferably 0 wt % to 5 wt %, more preferably 0 wt % to 3 wt %, still more preferably 0 wt % to 1 wt %.

A logarithmic standard deviation (σζ) of particle size distribution of the water-absorbing resin in accordance with the present invention is in a range of 0.20 to 0.50, preferably 0.25 to 0.40, more preferably 0.27 to 0.35.

In a case where the weight average particle diameter is smaller than the range of the present invention, the surface area of the water-absorbing resin becomes large and an acid odor is easily generated. In a case where the logarithmic standard deviation (σζ) of particle size distribution is large, an acid odor is easily generated and a water absorbing property is deteriorated.

(3-10) Initial Color Tone

An initial color tone of the water-absorbing resin of the present invention has, based on Hunter's Lab color system, an L-value of preferably 88 or more, more preferably 89 or more, still more preferably 90 or more. An upper limit is 100, and no problem occurs due to color tone, provided that the L-value is 88 or more. Moreover, an a-value is in a range of preferably −3 to 3, more preferably −2 to 2, still more preferably −1 to 1. Moreover, a b-value is in a range of preferably 0 to 12, more preferably 0 to 10, still more preferably 0 to 9. Note that, as the L-value approaches 100, whiteness is increased, and as the a-value and the b-value approach 0, the color fades and becomes substantially white.

(3-11) Color Tone with the Lapse of Time

A color tone with the lapse of time of the water-absorbing resin of the present invention has, based on the Hunter's Lab color system, an L-value of preferably 80 or more, more preferably 81 or more, still more preferably 82 or more, particularly preferably 83 or more. An upper limit is 100, and no problem occurs due to color tone, provided that the L-value is 80 or more. Moreover, an a-value is in a range of preferably −3 to 3, more preferably −2 to 2, still more preferably −1 to 1. Moreover, a b-value is in a range of preferably 0 to 15, more preferably 0 to 12, still more preferably 0 to 10. Note that, as the L-value approaches 100, whiteness is increased, and as the a-value and the b-value approach 0, the color fades and becomes substantially white.

(3-12) Average Sphericity

An average sphericity of the water-absorbing resin in accordance with the present invention is 0.65 or more, preferably in a range of 0.68 to 0.82, more preferably in a range of 0.70 to 0.80. In a case where the average sphericity is less than 0.65, a surface area is excessively enlarged and an acid odor is easily generated. On the other hand, in a case where the average sphericity is more than 0.82, it may be difficult to handle such a water-absorbing resin.

(3-13) Internal Gas Bubbles Ratio

An internal gas bubbles ratio of the water-absorbing resin in accordance with the present invention is controlled by gel-crush or the like to be in a range of preferably 0.1 to 3.0, more preferably 0.3 to 2.5, particularly preferably 0.5 to 2.0. From the viewpoint of physical property of the water-absorbing resin and reduction in odor, the internal gas bubbles ratio is preferably controlled to fall within the above described range so that fine powder is less generated by mechanical damage such as impact. Note that it is not preferable to control the internal gas bubbles ratio to be excessively small because (i) the manufacturing method (foaming polymerization, hot air drying, and the like) of the present invention cannot be used, (ii) a balance with the other physical properties is deteriorated, and (iii) the water absorbing speed (e.g., FSR) is decreased.

(3-14) Hydrophobic Solvent Content

A hydrophobic solvent content in the water-absorbing resin of the present invention is preferably less than 10 ppm, more preferably less than 5 ppm, still more preferably less than 1 ppm. Note that the hydrophobic solvent content is measured with, for example, a headspace gas chromatograph mass spectrometry or a detecting tube (for hydrocarbon).

[4] Purpose of Use of Polyacrylic Acid (Salt)-Based Water-Absorbing Resin

The purpose of use of the water-absorbing resin of the present invention is not limited to a particular one, and can preferably be used as an absorbent body of hygiene product such as a disposable diaper, a sanitary napkin, and an incontinence pad. In particular, the water-absorbing resin of the present invention can be used as an absorbent body of a high concentration disposable diaper (in which a large used amount of water-absorbing resin is contained in one (1) disposable diaper) that conventionally had a problem such as an odor derived from a raw material and coloring. Further, in a case where the water-absorbing resin of the present invention is used as an upper layer part of the absorbent body, it is possible to bring about remarkable effects.

Moreover, the absorbent body can contain an absorbent material such as pulp fibers, in addition to the water-absorbing resin. In this case, a content (i.e., core concentration) of the water-absorbing resin in the absorbent body is in a range of preferably 30 wt % to 100 wt %, more preferably 40 wt % to 100 wt %, still more preferably 50 wt % to 100 wt %, further still more preferably 60 wt % to 100 wt %, particularly preferably 70 wt % to 100 wt %, most preferably 75 wt % to 95 wt %.

By controlling the core concentration to fall within the above described range, in a case where the absorbent body is used as an upper layer part of an absorbent article, the absorbent article can maintain a clean white state. Further, such an absorbent body is excellent in diffusion property with respect to, for example, a body fluid such as urine and blood, and it is therefore possible to increase an absorption amount by efficient liquid distribution.

Note that the present invention also encompasses the following invention:

(1) A method for manufacturing a polyacrylic acid (salt)-based water-absorbing resin, the method including the steps of: (a) preparing a monomer aqueous solution containing acrylic acid (salt) as a main component; (b) carrying out polymerization on the monomer aqueous solution; (c) drying a water-containing gel-like cross-linked polymer obtained in the step (b); and (d) surface-crosslinking water-absorbing resin powder obtained after the step (c), the steps (a) through (d) being carried out in this order, an acetic acid content in acrylic acid or an acrylic acid aqueous solution, which is supplied in the step (a), being in a range of 300 ppm to 10000 ppm, and an acetic acid concentration lowering rate, which is defined by the following formula, being 30% or higher:

(Acetic acid concentration lowering rate) (%)={1−(acetic acid concentration in water-absorbing resin)/(acetic acid concentration in acrylic acid or acrylic acid aqueous solution)}×100 where "(acetic acid concentration in water-absorbing resin)" is an acetic acid concentration in the water-absorbing resin obtained as a product, and "(acetic acid concentration in acrylic acid or acrylic acid aqueous solution)" is an acetic acid concentration in the acrylic acid or the acrylic acid aqueous solution which is supplied in the step (a).

(2) The method described in the above (1), in which: the polymerization is foaming polymerization or grain refining polymerization in which the monomer aqueous solution has a concentration of solid content in a range of 30 wt % to 55 wt % and a degree of increase in solid content in the monomer aqueous solution is in a range of 1 wt % to 15 wt %; and acetic acid contained in the monomer aqueous solution is at least partially removed in the step (b).

(3) The method described in the above (1), in which: the polymerization is carried out on the monomer aqueous solution which has a concentration of solid content of lower than 30 wt %; and in and/or after the step (b), the method further includes the step of neutralizing the water-containing gel-like cross-linked polymer.

(4) The method described in any of the above (1) through (3), in which: a particulate water-containing gel-like cross-linked polymer, which is subjected to the step (c), is such that a weight average particle diameter (D50) of the particulate water-containing gel-like cross-linked polymer is in a range of 350 μm to 2000 μm, and a logarithmic standard deviation (σζ) of particle size distribution of the particulate water-containing gel-like cross-linked polymer is in a range of 0.2 to 1.5.

(5) The method described in any of the above (1) through (4), in which: in the step (c), acetic acid is at least partially removed by drying particulate water-containing gel-like cross-linked polymer, whose concentration of solid content is 50 wt % or lower, by hot air.

(6) The method as set forth in any of the above (1) through (5), in which: in the step (c), acetic acid is at least partially removed by adding a drying aid to particulate water-containing gel-like cross-linked polymer.

(7) The method described in any of the above (1) through (6), in which: in the step (c), acetic acid is at least partially removed by drying particulate water-containing gel-like cross-linked polymer at a drying temperature in a range of 165° C. to 230° C. for 5 minutes or more.

(8) The method described in any of (1) through (7), in which: in the step (c), acetic acid is at least partially removed (i) by controlling an ambient dewing point to be in a range of 50° C. to 100° C. during 50% or more of drying time or (ii) by reducing a pressure by 0.1% to 5% with respect to an atmospheric pressure during 50% or more of drying time.

(9) The method described in any of the above (1) through (8), in which: in the step (d), acetic acid is at least partially removed by carrying out surface-crosslinking in the presence of an acidic compound.

(10) The method described in any of the above (1) through (9), in which: in the step (d), acetic acid is at least partially removed by adding a surface crosslinking agent solution and then reducing the pressure by 0.1% to 5% with respect to the atmospheric pressure during 50% or more of heat treatment time.

(11) The method described in any of the above (1) through (10), further including the step of: (e) remoistening the water-absorbing resin, which has been obtained in the step (d), by carrying out heat treatment after adding 0.5 wt % to 15 wt % of water to the water-absorbing resin.

(12) The method described in the above (11), in which: in the step (e), a polyvalent metal ion is added.

(13) The method described in the above (11) or (12), in which: in the step (e), acetic acid is at least partially removed by setting (i) a temperature in heat treatment to 65° C. or higher and (ii) heat treatment time to 5 minutes or more.

(14) The method described in any of the above (11) through (13), in which: in the step (e), a moisture content in the water-absorbing resin is controlled to be in a range of 2 wt % to 9 wt %.

(15) The method described in any of the above (1) through (14), in which: an acetic acid content in the polyacrylic acid (salt)-based water-absorbing resin is in a range of 100 ppm to 2000 ppm.

(16) The method described in any of the above (1) through (15), in which acetic acid is removed by 10 wt % or more in and/or after the step (b).

(17) The method described in any of (1) through (16), in which a mixture of two or more types of acrylic acid or acrylic acid aqueous solution, which are different in acetic acid content, is used.

(18) The polyacrylic acid (salt)-based water-absorbing resin which has a saline flow conductivity (SFC) of 50 [×10$^{-7}$·s·cm$^3$·g$^{-1}$] or higher and an acetic acid content in a range of 100 ppm to 2000 ppm.

EXAMPLES

The following description will discuss the present invention more concretely in accordance with Examples and Comparative Examples below. Note, however, that the present invention is not limited to these and Example derived from a proper combination of technical means disclosed in respective different Examples is also encompassed in the technical scope of the present invention.

For convenience, a term "liter" may be abbreviated as "l" or "L", a term "% by weight" may be abbreviated as "wt %". Moreover, a value which is not higher than the detection limit in measuring a trace component is referred to as "N.D. (Non Detected)".

Note that a power source of an electric apparatus (including measurement of physical properties of the water-absorbing resin) used in Production Examples, Examples, and Comparative Examples was 200 V or 100 V, unless otherwise noted. Moreover, the physical properties of the water-absorbing resin of the present invention were measured at a room temperature (i.e., in a range of 20° C. to 25° C.) and at a relative humidity of 50% RH, unless otherwise noted.

[Measurement of Physical Properties of Water-Absorbing Resin]

(a) Water absorption capacity without load (CRC)

The water absorption capacity without load (CRC) of the water-absorbing resin of the present invention was measured in conformity to ERT441.2-02.

(b) Water absorption capacity under load (AAP) The water absorption capacity under load (AAP) of the water-absorbing resin of the present invention was measured substantially in conformity to ERT442.2-02, except that a load condition was changed to 4.83 kPa (0.7 psi).

(c) Saline Flow Conductivity (SFC)

The saline flow conductivity (SFC) of the water-absorbing resin of the present invention was measured in accordance with a measuring method disclosed in the specification of U.S. Pat. No. 5,669,894.

(d) Moisture Content, Concentration of Solid Content

A moisture content of each of the water-absorbing resin and the water-containing gel-like cross-linked polymer in the present invention was measured substantially in conformity to ERT430.2-02, except that a weight of the water-absorbing resin was changed from 4.0 g to 1.0 g and a drying temperature was changed from 105° C. to 180° C. Note that the water-containing gel-like cross-linked polymer is used which has been crushed into a state of particles.

Note that the concentration of solid content (wt %) is defined as (100−moisture content) (wt %).

(e) Residual Monomer (Quantitative Determination of Trace Component)

The residual monomer in the water-absorbing resin of the present invention was measure in conformity to ERT410.2-02. Note that trace components (e.g., acetic acid) other than the residual monomer were also measured in conformity to ERT410.2-02.

Moreover, trace components (e.g., acetic acid) in the water-containing gel-like cross-linked polymer were measured while changing (i) a weight of a sample to 2 g and (ii) a stirring time to 24 hours.

(f) Water Soluble Component

The water soluble component of the water-absorbing resin of the present invention was measured in conformity to ERT470.2-02.

(g) Water Absorbing Speed (FSR)

The water absorbing speed (FSR) of the water-absorbing resin of the present invention was measured with the following method:

That is, 1.00 g of the water-absorbing resin was poured into 25 ml glass beaker (having diameter in a range of 32 mm to 34 mm, height of 50 mm) such that an upper surface of the water-absorbing resin is leveled. Note that, in this case, it is possible to carry out an operation such as tapping a bottom of the beaker.

Next, 20 g of a 0.90 wt % of sodium chloride aqueous solution, whose temperature has been adjusted to 23±0.2° C., was poured into a 50 ml glass beaker, and a total weight (W1) (g) of the beaker and the sodium chloride aqueous solution was measured. Then, the sodium chloride aqueous solution was poured quickly and gently into the beaker containing the water-absorbing resin, and a time required for the entire sodium chloride aqueous solution to be absorbed by the water-absorbing resin was measured.

Note that the time was measured from a time point at which the sodium chloride aqueous solution made contact with the water-absorbing resin to a time point at which the upper surface, which had first been the sodium chloride aqueous solution, was replaced with the water-absorbing resin that had absorbed the entire sodium chloride aqueous solution. The time thus measured is represented as "ts" (second). Moreover, the replacement in the upper surface was confirmed visually in an angle of 20° with respect to the vertical direction.

Lastly, a weight (W2) (g) of the 50 ml glass beaker, which had been emptied, was measured, and the water absorbing speed (FSR) was calculated based on Formula 5 below.

[Math. 6]

$$FSR[g/g/s] = (W1 - W2)/(\text{weight of water-absorbing resin})/ts \quad \text{Formula 5}$$

(h) Particle Size

The particle size of the water-absorbing resin in accordance with the present invention is measured with the use of a standard sieve in conformity to measuring methods disclosed in International Publication No. 2004/69915 and EDANA ERT420.2-02. Note that types of standard sieve can be added as appropriate and, in the present invention, standard sieves were used which had respective mesh sizes of 850 μm, 710 μm, 600 μm, 500 μm, 425 μm, 300 μm, 212 μm, 150 μm, and 45 μm.

Moreover, the weight average particle diameter (D50) and the particle diameter distribution range are measured with a method similar to the method described in the specification of U.S. Pat. No. 7,638,570, columns 27 and 28, "(3) Mass-Average Particle Diameter (D50) and Logarithmic Standard Deviation (σζ) of Particle Diameter Distribution".

(i) Sensory Evaluation 1 (Evaluation of Odor from Water-Absorbing Resin Swollen with Physiological Saline Solution)

A sensory evaluation 1 (evaluation of odor) on the water-absorbing resin of the present invention was carried out with the following procedures:

That is, 50 ml of a 0.9 wt % of sodium chloride aqueous solution was poured into a 120 ml polypropylene container having a lid (product name: Pack Ace/manufactured by: Teraoka Co., Ltd./size: aperture diameter of 50 mm×bottom diameter of 54 mm×height of 74 mm).

Next, 2.0 g of the water-absorbing resin was added into the polypropylene container containing the sodium chloride aqueous solution so that the water-absorbing resin absorbs the sodium chloride aqueous solution. After that, the container was covered with the lid and then maintained at 37° C. for 6 hours.

After the maintaining time (i.e., 6 hours) elapsed, the lid of the container was opened, and the odor of the water-absorbing resin was evaluated in accordance with the following standard by smelling at a location 3 cm above an opening of the container.

The evaluation of odor of the water-absorbing resin was carried out by 10 adults who were arbitrarily selected. Each of the adults evaluated odor with the following 5 levels, i.e., "1: odorless", "2: slight odor", "3: perceivable and permissible odor", "4: strong odor", and "5: extraordinary odor". Then, the odor of the water-absorbing resin was evaluated based on an average of values obtained from the 10 adults.

(j) Sensory Evaluation 2 (Evaluation of Odor of Water-Absorbing Resin Swollen with Artificial Urine)

The sensory evaluation 2 on the water-absorbing resin of the present invention was different from the (i) sensory evaluation 1 in that artificial urine was absorbed by the water-absorbing resin instead of the physiological saline solution. The artificial urine used was so-called Jayco artificial urine (USA; available from Jayco, Inc.) [composition: 2.0 g of potassium chloride, 2.0 g of sodium sulfate, 0.85 g of ammonium dihydrogen phosphate, 0.15 g of ammonium monohydrogen phosphate, 0.19 g of calcium chloride, and 0.23 g of magnesium chloride as anhydrous salts; and distilled water, where a total amount was 1000 g].

(k) Quantitative Determination of Trace Component in Acrylic Acid

Quantitative determination of trace components contained in acrylic acid used as a raw material for the water-absorbing resin of the present invention was carried out with gas chromatography. As a detector, a flame ionization detector (FID) was used. Note that the measuring method makes it possible to quantitatively determine acetic acid and propionic acid, and a detection limit is 1 ppm.

Moreover, from a chromatograph obtained by the measurement, it is possible to quantitatively determine acetic acid in the acrylic acid or acrylic acid aqueous solution on the acrylic acid basis. The same applies to the other trace components.

(l) Apparent Density

An apparent density of the water-absorbing resin of the present invention was measured in accordance with a method described in "Apparent Density" on page 26 of US Patent Application Publication No. 2012/0258851 (corresponding JP Patent Literature: International Publication No. 2011/78298 pamphlet).

(m) Real Density

A real density of the water-absorbing resin of the present invention was measured in accordance with a method described in "Real Density" on page 26 of US Patent Application Publication No. 2012/0258851 (corresponding JP Patent Literature: International Publication No. 2011/78298 pamphlet).

(n) Internal Gas Bubbles Ratio

An internal gas bubbles ratio of the water-absorbing resin of the present invention was calculate based on the following formula with the use of the apparent density (which is assumed as $\rho 1$ [g/cm$^3$]) measured with the method described in the above [Apparent density] and the real density (which is assumed as $\rho 2$ [g/cm$^3$]) measured with the method described in the above [Real density].

(Internal gas bubbles ratio) [%]={(real density)−(apparent density)}/(real density)×100

(p) Average Sphericity

A sphericity (SPHT) was obtained as follows: an image of the water-absorbing resin was obtained with the use of a microscope (with magnification of 10 times) and then a circularity and a sphere volume of each particle were obtained with the use of an image analysis software (WinROOF Ver. 6.1.1). In this specification, the average sphericity indicates a (volume) average sphericity weighted with a sphere volume which has been obtained from a diameter that is a shortest width of a polymer particle as above described.

Specifically, water-absorbing resin, which had no segregation, was extracted with a micro spatula and dispersed on a tray whose bottom surface was black and flat. In this case, in a case where the particles of the water-absorbing resin were making contact with each other, the tray was tapped so that the particles were dispersed to be away from each other.

Next, an image of the water-absorbing resin on the tray was obtained with the use of a microscope (with magnification of 10 times) with a pixel number of 100 thousand to 1 million pixels per 1 mm$^2$. From the image, a circularity and a sphere volume of each of the particles of the water-absorbing resin were obtained with the use of the image analysis software. Here, "circularity" is a synonymous of "sphericity" in this specification. In a case where the number of particles was less than 100, an image of the water-absorbing resin was taken again with the microscope and analyzed with the image analysis software, and then data thus analyzed was added so that the circularity and the sphere volume were obtained for each of the 100 or more particles of the water-absorbing resin. From these pieces of data, the (volume) average sphericity weighted with the sphere volume was calculated.

Production Example 1

Gaseous acrylic acid obtained by contact vapor-phase oxidation of propylene was captured by using water, thereby continuously obtaining a 70 wt % of acrylic acid aqueous solution. Then, an azeotropic dehydration distillation was performed by using a distillation column (azeotropic dehydration column) equipped with 50 stages of perforated-plates with no weir. In the azeotropic dehydration distillation, toluene was supplied from a top of the distillation column (azeotropic dehydration column), and the acrylic acid aqueous solution was supplied to one of middle stages of the distillation column. As a result of the azeotropic dehydration, crude acrylic acid was obtained from a bottom of the distillation column.

Next, the crude acrylic acid was distilled at a reflux ratio of 1 with a distillation column (high-boiling-point impurity removing column) to a bottom of which the crude acrylic acid was continuously supplied, and which was equipped with 50 stages of perforated-plates with no weir. After this distillation, the crude acrylic acid was purified by re-distillation, and mixed with p-methoxy phenol serving as a polymerization inhibitor. As a result, an acrylic acid composition (a1) whose purity was 99 wt % or greater was obtained.

Impurities remained in the acrylic acid composition (a1) included 300 ppm of acetic acid, 100 ppm of propionic acid, 100 ppm of acrylic dimer, and N.D. amounts (not detectable amounts/1 ppm or less) of protoanemonin (PAN) and aldehyde content. Moreover, p-methoxy phenol content in the acrylic acid composition was 70 ppm.

Production Example 2

The above operation was repeated in the same manner as in Production Example 1 except that an azeotropic dehydration column used herein had 45 stages, instead of 50 stages, of perforated-plates with no weir. This produced an acrylic acid composition (a2), whose purity was 99 wt % or greater.

Impurities remained in the acrylic acid composition (a2) included 1800 ppm of acetic acid, 400 ppm of propionic acid, 110 ppm of acrylic dimer, and N.D. amounts (not detectable amounts/1 ppm or less) of protoanemonin (PAN) and aldehyde content. Moreover, p-methoxy phenol content in the acrylic acid composition was 70 ppm.

Production Example 3

The acrylic acid composition (a1) obtained in Production Example 1 and the acrylic acid composition (a2) obtained in Production Example 2 at a weight ratio of 2:3 were fed and mixed in a same tank, in which a mixture thus obtained was held for an average holding time of 4 hours and collected thereafter, thereby obtaining an acrylic acid composition (a3).

Impurities remained in the acrylic acid composition (a3) included 1200 ppm of acetic acid, 280 ppm of propionic acid, 120 ppm of acrylic dimer, and N.D. amounts (not detectable amounts/1 ppm or less) of protoanemonin (PAN) and aldehyde content. Moreover, p-methoxy phenol content in the acrylic acid composition was 70 ppm.

Production Example 4

The 70 wt % of acrylic acid aqueous solution obtained in Production Example 1 was crystalized out, thereby obtaining an acrylic acid composition (a4). Impurities remained in the acrylic acid composition (a4) included 1470 ppm of acetic acid, 270 ppm of propionic acid, 90 ppm of acrylic dimer, and N.D. amounts (not detectable amounts/1 ppm or less) of protoanemonin (PAN) and aldehyde content. Moreover, p-methoxy phenol content in the acrylic acid composition was adjusted to 70 ppm by adding p-methoxy phenol.

Comparative Example 1

Into the acrylic acid composition (a3) obtained in Production Example 3, commercially-available propionic acid (made by Tokyo Chemical Industry Co., Ltd./Product code; P0500) was added, thereby adjusting the propionic content to 300 ppm as in Example 3 in Patent Literature (US patent application publication No. 2008/214750) meanwhile the acetic acid content was 1200 ppm. An acrylic acid composition thus obtained is denoted as an acrylic acid composition (a3+ProA) hereinafter.

By using the acrylic acid composition (a3+ProA), a monomer aqueous solution of 75 mol % in neutralization rate was prepared in the same manner as in Example 3 of Patent Literature 12, thereby obtaining a comparative water-absorbing resin (c1).

Specifically, polymerization was conducted in the same manner as in the operation of Example 3 of Patent Literature 12 by using a jacketed kneader of 10 L in capacity. Consequently, a comparative water-containing gel-like cross-linked polymer (c1) in the form of particles was obtained with a concentration of solid content of 37 wt %.

The comparative water-containing gel-like cross-linked polymer (c1) in the form of particles was further treated as follows even though the following treatment is not specifically described in Patent Literature 12. The comparative water-containing gel-like cross-linked polymer (c1) in the form of particles was scattered over a drying mesh to be accumulated by about 1 g/cm$^2$ (to be about 2 cm in layer height) on the drying mesh. Then, the comparative water-containing gel-like cross-linked polymer (c1) was dried by using a well-known through-flow type stationary dryer (made by Satake Chemical Equipment MFG. Ltd. (Product Code; 71-S6)), thereby obtaining a comparative dried polymer (c1).

Then, the comparative dried polymer (c1) is pulverized by using a roll mill with roll clearance of 0.4 mm, and classified by using JIS standard sieves of 850 μm and 100 μm in mesh size, respectively, thereby obtaining comparative water-absorbing resin powder (c1) in a range of 100 μm to 850 μm in particle diameter. The comparative water-absorbing resin powder (c1) thus obtained was 3.9 wt % in moisture content, 38 g/g in CRC, and 10 wt % in water soluble component.

The comparative water-absorbing resin powder (c1) was further subjected to surface crosslinking treatment according to the method in Example 3 of Patent Literature 12, thereby obtaining comparative water-absorbing resin (c1).

Physical properties of the comparative water-absorbing resin (c1) thus obtained are shown in Tables 1 and 2.

In the steps of the water-absorbing resin manufacturing process herein, acetic acid removing rates were as follows: approximately 0% in the polymerization step (the acetic acid concentration 350 ppm was constant against moisture content change from 64 wt % to 63 wt %), 7% in the drying step (the acetic acid concentration was changed from 350 ppm to 870 ppm against moisture content change from 63 wt % to 4.0 wt %), approximately 0% in the surface crosslinking step (the acetic acid concentration was changed from 870 ppm to 860 ppm against moisture content change from 4.0 wt % to 5.1 wt %), and substantially 0% in the other steps (such as pulverization and classification), with 7% throughout the overall manufacturing process. Moreover, in comparison with the acetic acid concentration (1200 ppm) in the acrylic acid composition (a3+ProA) used in the polymerization, the acetic acid concentration in the comparative water-absorbing resin (c1) was 860 ppm, and thus acetic acid concentration lowering rate was 28.3% (=(1−860/1200)×100).

Example 1

Continuously fed and mixed in a mixer were 216 parts by weight of the acrylic acid composition thus obtained in Production Example 2 (a2/acetic acid concentration 1800 ppm), 186 parts by weight of a 48.5 wt % of sodium hydroxide aqueous solution, 186 parts by weight of pure water, 12.5 parts by weight of a 10 wt % of polyethylene glycol diacrylate (n=9) aqueous solution, and 5.3 parts by weight of a 1 wt % of ethylene diamine tetramethylene phosphate aqueous solution. Thereby, a monomer aqueous solution (1) was obtained, which had a neutralization rate of 75 mol %, and concentration of 43 wt %. The sodium hydroxide aqueous solution had an iron content of 3 ppm (based on $Fe_2O_3$/measured value). In comparison with acrylic acid (molecular weight 72), an average molecular weight of the monomer was 88.5. Here, the acetic acid concentration was diluted.

Subsequently, the monomer aqueous solution (1) was heated by using a heater. When the temperature of the monomer aqueous solution (1) reached 95° C., 12 parts by weight of a 3 wt % of sodium persulfate aqueous solution was added therein. Then, the monomer aqueous solution (1) was poured over a trough plate coated with Teflon (registered trademark), thereby spontaneously starting polymerization. The polymerization proceeded while boiling the monomer aqueous solution (1) vigorously on the trough plate.

In this manner, a water-containing gel-like cross-linked polymer (1) in the form of sheet (thickness; about 1 mm to 5 mm) was obtained. A concentration of solid content of the water-containing gel-like cross-linked polymer (1) in the form of sheet was measured to be 53 wt %, increasing by 10 wt % from the concentration of solid content (43 wt %) of the monomer aqueous solution after the addition of the sodium persulfate aqueous solution.

Next, the water-containing gel-like cross-linked polymer (1) in the form of sheet was subjected to gel-crushing by being fed into a meat chopper (made by Hiraga Koushakusho) equipped with a porous die of 6 mm in pore diameter while adding water together. The gel-crush produced water-containing gel-like cross-linked polymer (1) in the form of particles. The water-containing gel-like cross-linked polymer (1) in the form of particles thus obtained was 50 wt % in concentration of solid content, 976 μm in weight average particle diameter (D50), and 0.96 in logarithmic standard deviation (σζ) of particle size distribution.

Subsequently, the water-containing gel-like cross-linked polymer (1) in the form of particles was scattered over a drying mesh to be accumulated by about 1 g/cm² (with a layer height of about 2 cm) on the drying mesh. Then, the water-containing gel-like cross-linked polymer (1) in the form of particles was dried by being fed to a through-flow type stationary dryer (made by Satake Chemical Equipment MFG. Ltd. (through-flow type batch dryer; Product Code; 71-S6)), thereby obtaining a dried polymer (1). The drying was conducted at a drying temperature of 180° C. for drying time of 50 minutes with an ambient dewing point inside the dryer adjusted to 70° C. by blowing steam into the dryer.

After that, the dried polymer (1) was pulverized by using a roll mill (with roll clearance of 1 mm/0.7 mm/0.45 mm), and then classified with JIS standard sieves of 850 μm and 150 μm in mesh size, thereby obtaining water-absorbing resin powder (1). The water-absorbing resin powder (1) thus obtained was 3.6 wt % in moisture content, 36 g/g in CRC, and 9.2 wt % in water soluble component.

Next, in a ploughshare mixer of 5 L capacity (made by Loedige), 500 g of the water-absorbing resin powder (1) was supplied and stirred, which was then sprayed and mixed with a surface crosslinking agent solution, being made up of 20 g of water, 4 g of propylene glycol, and 1 g of ethylene glycol diglycidyl ether, thereby obtaining a moistened mixture (1).

Then, in a mortar mixer (Nishinihon Shikenki Co., Ltd.), the mixture (1) was fed and heated (heating (oil bath) temperature; 120° C., heating time; 30 min). After that, 1 g of silica (made by Nippon Aerosil Co., Ltd./Product name; Aerosil 200) was added in and mixed with the mixture (1), thereby obtaining water-absorbing resin (S1). Physical properties of the water-absorbing resin (S1) thus obtained are shown in Tables 1 and 2.

In the steps of the water-absorbing resin manufacturing process herein, acetic acid removing rates were as follows: 12% in the polymerization step (the acetic acid concentration was changed from 630 ppm to 680 ppm against moisture content change from 57 wt % to 47 wt %), 7% in the drying step (the acetic acid concentration was changed from 680 ppm to 1150 ppm against moisture content change from 47 wt % to 3.6 wt %), approximately 0% in the surface crosslinking step (the acetic acid concentration was changed from 1150 ppm to 1130 ppm against moisture content change from 3.6 wt % to 5.3 wt %), and substantially 0% in the other steps (as in Example 2 and other Examples described below), with 18% throughout the overall manufacturing process. Moreover, in comparison with the acetic acid concentration (1800 ppm) in the acrylic acid used in the polymerization, the acetic acid concentration in the water-absorbing resin (S1) thus obtained was 1130 ppm, and acetic acid concentration lowering rate was 37.2% (=(1−1130/1800)×100).

Example 2

Water-absorbing resin powder (2) was prepared in the same manner as in Example 1, except that, instead of the acrylic acid composition (a2), the acrylic acid composition (a3) being obtained in Production Example 3 with acetic acid concentration of 1200 ppm was used. The water-absorbing resin powder (2) thus obtained was 3.8 wt % in moisture content, 34 g/g in CRC, and 8.3 wt % in water soluble component.

Next, the water-absorbing resin powder (2) was added and mixed with the surface crosslinking agent solution and silica as used in Example 1, thereby obtaining water-absorbing resin (S2). Physical properties of the water-absorbing resin (S2) thus obtained are shown in Tables 1 and 2.

In the steps of the water-absorbing resin manufacturing process herein, acetic acid removing rates were as follows similarly to Example 1: 12% in the polymerization step (the acetic acid concentration was changed from 420 ppm to 460 ppm against moisture content change from 57 wt % to 47 wt %), 7% in the drying step (the acetic acid concentration was changed from 460 ppm to 770 ppm against moisture content change from 47 wt % to 3.8 wt %), and approximately 0% in the surface crosslinking step (the acetic acid concentration was changed from 770 ppm to 760 ppm against moisture content change from 3.8 wt % to 5.2 wt %), with 18% throughout the overall manufacturing process. Moreover, in comparison with the acetic acid concentration (1200 ppm) in the acrylic acid used in the polymerization, the acetic acid concentration in the water-absorbing resin (S2) thus obtained was 760 ppm, and thus acetic acid concentration lowering rate was 36.7% (=(1−760/1200)×100).

Example 3

Water-absorbing resin (S3) was prepared in the same manner as in Example 1 except that, instead of the surface crosslinking agent solution, 15 g of water, 3.5 g of propylene glycol, and 1.5 g of 1,4-butanediol were used, the heating process was carried out at a heating temperature of 200° C. for 40 min under a slightly-reduced pressure lower than atmospheric pressure by 0.2%, 5 g of a 27 wt % of aluminum sulfate aqueous solution was used instead of silica, and the mixing temperature was 80° C. Physical properties of the water-absorbing resin (S3) thus obtained are shown in Tables 1 and 2.

In the steps of the water-absorbing resin manufacturing process herein, acetic acid removing rates were as follows: 12% in the polymerization step (the acetic acid concentration was changed from 630 ppm to 680 ppm against moisture content change from 57 wt % to 47 wt %), 7% in the drying step (the acetic acid concentration was changed from 680 ppm to 1150 ppm against moisture content change from 47 wt % to 3.6 wt %), 1% in the surface crosslinking step (the acetic acid concentration was changed from 1150 ppm to 1170 ppm against moisture content change from 3.6 wt % to 1.5 wt %), and substantially 0% in the other steps, with 19% throughout the overall manufacturing process. Moreover, in comparison with the acetic acid concentration (1800 ppm) in the acrylic acid used in the polymerization, the acetic acid concentration in the water-absorbing resin (S3) thus obtained was 1150 ppm, and thus acetic acid concentration lowering rate was 36.1% (=(1−1150/1800)×100).

Example 4

Water-absorbing resin powder (4) was prepared in the same manner as in Example 3, except that 171 parts by weight of a 48.5 wt % of sodium hydroxide aqueous solution and 191 parts by weight of pure water were used (neutralization rate was 69 mol %). The water-absorbing resin powder (4) thus obtained was 4.6 wt % in moisture content, 32 g/g in CRC, and 7.6 wt % in water soluble component.

Next, the water-absorbing resin powder (4) was added and mixed with the surface crosslinking agent solution and aluminum sulfate aqueous solution as used in Example 3, thereby obtaining water-absorbing resin (S4). Physical properties of the water-absorbing resin (S4) thus obtained are shown in Tables 1 and 2.

In the steps of the water-absorbing resin manufacturing process herein, acetic acid removing rates were as follows: 11% in the polymerization step (the acetic acid concentration was changed from 640 ppm to 700 ppm against moisture content change from 57 wt % to 47 wt %), 10% in the drying step (the acetic acid concentration was changed from 700 ppm to 1130 ppm against moisture content change from 47 wt % to 4.6 wt %), 1% in the surface crosslinking step (the acetic acid concentration was changed from 1130 ppm to 1160 ppm against moisture content change from 4.6 wt % to 1.4 wt %), and substantially 0% in the other steps, with 21% throughout the overall manufacturing process. Moreover, in comparison with the acetic acid concentration (1800 ppm) in the acrylic acid used in the polymerization, the acetic acid concentration in the water-absorbing resin (S4) thus obtained was 1150 ppm, and acetic acid concentration lowering rate was 36.1% (=(1−1150/1800)×100).

Example 5

Water-absorbing resin (S5) was prepared in the same manner as in Example 1 except that the heating was performed by using steam. Physical properties of the water-absorbing resin (S5) thus obtained are shown in Tables 1 and 2.

In the steps of the water-absorbing resin manufacturing process herein, acetic acid removing rates were as follows similarly to Example 1: 12% in the polymerization step, 7% in the drying step, 1% in the surface crosslinking step (the acetic acid concentration was changed from 1150 ppm to 1100 ppm against moisture content change from 3.6 wt % to 7.4 wt %), and substantially 0% in the other steps, with 19% throughout the overall manufacturing process. Moreover, in comparison with the acetic acid concentration (1800 ppm) in the acrylic acid used in the polymerization, the acetic acid concentration in the water-absorbing resin (S5) thus obtained was 1100 ppm, and thus acetic acid concentration lowering rate was 38.9% (=(1−1100/1800)×100).

Example 6

An acrylic acid composition (a2) thus obtained in Production Example 2 was mixed with commercially-available acetic acid (made by Wako Pure Chemical Industries, Ltd./Reagent Special Grade; distributer code 017-00256), thereby obtaining an acrylic acid composition (a2+AcOH) with acetic acid content (acetic acid concentration) of 7000 ppm.

Water-absorbing resin powder (6) was prepared from the acrylic acid composition (a2+AcOH) in the same manner as in Example 1. The water-absorbing resin powder (6) thus obtained was 4.1 wt % in moisture content, 35 g/g in CRC, and 8.5 wt % in water soluble component.

Next, the water-absorbing resin powder (6) was added and mixed with the surface crosslinking agent solution and silica as used in Example 1, thereby obtaining water-absorbing resin (S6). Physical properties of the water-absorbing resin (S6) thus obtained are shown in Tables 1 and 2.

In the steps of the water-absorbing resin manufacturing process herein, acetic acid removing rates were as follows similarly to Example 1: 12% in the polymerization step (the acetic acid concentration was changed from 2450 ppm to 2660 ppm against moisture content change from 57 wt % to 47 wt %), 7% in the drying step (the acetic acid concentration was changed from 2660 ppm to 4470 ppm against moisture content change from 47 wt % to 4.1 wt %), approximately 0% in the surface crosslinking step (the acetic acid concentration was changed from 4470 ppm to 4420 ppm against moisture content change from 4.1 wt % to 5.3 wt %), and substantially 0% in the other steps, with 18% throughout the overall manufacturing process. Moreover, in comparison with the acetic acid concentration (7000 ppm) in the acrylic acid used in the polymerization, the acetic acid concentration in the water-absorbing resin (S6) thus obtained was 4420 ppm, and acetic acid concentration lowering rate was 36.9% (=(1−4420/7000)×100).

Comparative Example 2

An acrylic acid composition (a2) thus obtained in Production Example 2 was mixed with commercially-available acetic acid (made by Wako Pure Chemical Industries, Ltd./Reagent Special Grade; Distributer code 017-00256), thereby obtaining an acrylic acid composition (c2) with acetic acid content (acetic acid concentration) of 12000 ppm.

Water-absorbing resin powder (c2) was prepared from the acrylic acid composition (c2) in the same manner as in Example 1. The water-absorbing resin powder (c2) thus obtained was 4.4 wt % in moisture content, 35 g/g in CRC, and 11.5 wt % in water soluble component.

Next, the water-absorbing resin powder (c2) was added and mixed with the surface crosslinking agent solution and silica as used in Example 1, thereby obtaining water-absorbing resin (c2). Physical properties of the water-absorbing resin (c2) thus obtained are shown in Tables 1 and 2.

In the steps of the water-absorbing resin manufacturing process herein, acetic acid removing rates were as follows: 12% in the polymerization step (the acetic acid concentration was changed from 4200 ppm to 4550 ppm against moisture content change from 57 wt % to 47 wt %), 7% in the drying step (the acetic acid concentration was changed from 4550 ppm to 7660 ppm against moisture content change from 47 wt % to 4.4 wt %), and approximately 0% in the surface crosslinking step (the acetic acid concentration was changed from 7660 ppm to 7590 ppm against moisture content change from 4.4 wt % to 5.2 wt %), with 17% throughout the overall manufacturing process. Moreover, in comparison with the acetic acid concentration (12000 ppm) in the acrylic acid used in the polymerization, the acetic acid concentration in the water-absorbing resin (c2) thus obtained was 7590 ppm, and thus acetic acid concentration lowering rate was 36.8% (=(1−7590/12000)×100).

Comparative Example 3

An acrylic acid composition (a2) thus obtained in Production Example 2 was mixed with commercially-available acetic acid (made by Wako Pure Chemical Industries, Ltd./Reagent Special Grade; Distributer code 017-00256), thereby obtaining an acrylic acid composition (c3) with acetic acid content (acetic acid concentration) of 18000 ppm.

Water-absorbing resin powder (c3) was prepared from the acrylic acid composition (c3) in the same manner as in Example 1. The water-absorbing resin powder (c3) thus obtained was 4.0 wt % in moisture content, 35 g/g in CRC, and 13.05 wt % in water soluble component.

Next, the water-absorbing resin powder (c3) was added and mixed with the surface crosslinking agent solution and silica as used in Example 1, thereby obtaining water-absorbing resin (c3). Physical properties of the water-absorbing resin (c3) thus obtained are shown in Tables 1 and 2.

In the steps of the water-absorbing resin manufacturing process herein, acetic acid removing rates were as follows: 12% in the polymerization step (the acetic acid concentration was changed from 6300 ppm to 6830 ppm against moisture content change from 57 wt % to 47 wt %), 7% in the drying step (the acetic acid concentration was changed from 6830 ppm to 11530 ppm against moisture content change from 47 wt % to 4.0 wt %), and approximately 0% in the surface crosslinking step (the acetic acid concentration was changed from 11530 ppm to 11350 ppm against moisture content change from 4.0 wt % to 5.3 wt %), with 17% throughout the overall manufacturing process. Moreover, in comparison with the acetic acid concentration (18000 ppm) in the acrylic acid used in the polymerization, the acetic acid concentration in the water-absorbing resin (c3) thus obtained was 11350 ppm, and thus acetic acid concentration lowering rate was 36.9% (=(1−11350/18000)×100).

Comparative Example 4

According to Example 1 of Patent Literature 11 (Japanese Patent Application Publication, Tokukai, No. 2012-31292), reverse-phase polymerization, azeotropic dehydration, filtration, and drying were performed, thereby obtaining comparative water-absorbing resin (c4) with an acetic acid removing rate of 32% in the overall water-absorbing resin manufacturing process herein. The comparative water-absorbing resin (c4) was 10 wt % in moisture content, 31 [g/g] in CRC, and 4 wt % in water soluble component. Moreover, in comparison with propionic acid amount (12000 ppm) and acetic acid amount (500 ppm) in the acrylic acid used in the polymerization, the comparative water-absorbing resin (c4) thus obtained was 0.25 wt % in propionic acid concentration, and 250 ppm in acetic acid concentration. Thus, an acetic acid lowering rate of the comparative water-absorbing resin (c4) was 50%.

Comparative Example 5

In order to find out how much acetic acid would be removed by well-known foaming polymerization with acrylic acid containing a large quantity of acetic acid, an experiment was conducted in accordance with Comparative Example 4 of Patent Literature 11 (Japanese Patent Application Publication, Tokukai, No. 2012-31292), thereby obtaining comparative water-absorbing resin (c5).

Specifically, in accordance with the operation in Example 4 of Patent Literature 11, effervescent aqueous solution polymerization was conducted with acrylic acid having propionic acid content (propionic acid concentration) of 1.2 wt % and acetic acid content (acetic acid concentration) of 500 ppm. A water-containing gel-like cross-linked polymer thus obtained was grain-refined by using a meat chopper, thereby obtaining a comparative water-containing gel-like cross-linked polymer (c5) in the form of particles. The comparative water-containing gel-like cross-linked polymer (c5) in the form of particles thus obtained was 55 wt % in concentration of solid content, 1150 μm in weight average particle diameter (D50), and 1.63 in logarithmic standard deviation (σζ) of particle size distribution.

The comparative water-containing gel-like cross-linked polymer (c5) in the form of particles was further treated as follows even though the following treatment is not specifically described in Patent Literature 11. The comparative water-containing gel-like cross-linked polymer (c5) in the form of particles was scattered over a drying mesh to be accumulated by about 1 g/cm$^2$ (to be about 2 cm in layer height) on the drying mesh. Then, the comparative water-containing gel-like cross-linked polymer (c5) was dried at 200° C. for 40 min by using a well-known through-flow type stationary dryer (made by Satake Chemical Equipment MFG. Ltd. (Product Code; 71-S6)), thereby obtaining a comparative dried polymer (c5).

Then, the comparative dried polymer (c5) was pulverized by using a roll mill with roll clearance of 0.4 mm, and classified by using JIS standard sieves of 850 μm and 150 μm in mesh size, respectively, thereby obtaining comparative water-absorbing resin powder (c5) in a range of 150 μm to 850 μm in particle diameter.

The comparative water-absorbing resin powder (c5) thus obtained was 2.4 wt % in moisture content, 35.8 g/g in CRC, and 9.2 wt % in water soluble component. The comparative water-absorbing resin powder (c5) as such was regarded as comparative water-absorbing resin (c5). Physical properties of the comparative water-absorbing resin (c5) thus obtained are shown in Tables 1 and 2.

In the steps of the water-absorbing resin manufacturing process herein, acetic acid removing rates were as follows: 12% in the polymerization step (the acetic acid concentration was changed from 190 ppm to 200 ppm against moisture content change from 55 wt % to 45 wt %), and 5% in the drying step (the acetic acid concentration was changed from 200 ppm to 340 ppm against moisture content change from 45 wt % to 2.4 wt %), with 16% throughout the overall manufacturing process. Moreover, in comparison with the acetic acid concentration (500 ppm) and propionic acid content (1.2%) in the acrylic acid used in the polymerization, the acetic acid concentration in the comparative water-absorbing resin (c5) thus obtained was 340 ppm, and thus acetic acid concentration lowering rate was 33%. Propionic acid removing rates were also calculated in the same manner as in the acetic acid removing rate calculation, except that acetic acid was replaced with propionic acid. The propionic acid removing rates were 35% in the polymerization step, and 15% in the drying step, with 45% throughout the overall manufacturing process of the comparative water-absorbing resin (c5). Thus, removing rate of acetic acid/propionic acid in total was 44%. This indicates that acetic acid (removing rate 16%) is more difficult to remove, compared with propionic acid (removing rate 45%).

Example 7

The operation in Example 1 was repeated, except that the drying step was changed as follows, thereby obtaining water-absorbing resin powder (7), and water-absorbing resin (S7).

The drying step herein was conducted under such conditions that the water-containing gel-like cross-linked polymer (c1) in the form of particles was subjected to blowing of over-heated steam of 120° C. for 10 minutes in a microwave oven "Healsio" (made by Sharp Corporation, product code: AX-GX2) in a water oven mode (after preheated), and then dried at 180° C. for 30 minutes by using a through-flow type stationary dryer (made by Satake Chemical Equipment MFG. Ltd. (through-flow type batch dryer; Product Code; 71-S6)). Temperature of the water-containing gel-like cross-linked polymer in the form of particles after being subjected to the blow of over-heated steam was about 80° C.

The water-absorbing resin powder (7) thus obtained was 4.1 wt % in moisture content, 37 g/g in CRC, and 9.7 wt % in water soluble component.

In the steps of the water-absorbing resin manufacturing process herein, acetic acid removing rates were as follows: 12% in the polymerization step (the acetic acid concentration was changed from 630 ppm to 680 ppm against moisture content change from 57 wt % to 47 wt %), 31% in the drying step (the acetic acid concentration was changed from 680 ppm to 860 ppm against moisture content change from 47 wt % to 4.1 wt %), and approximately 0% in the surface crosslinking step (the acetic acid concentration was changed from 850 ppm to 840 ppm against moisture content change from 4.1 wt % to 5.3 wt %), with 39% throughout the overall manufacturing process. Moreover, in comparison with the acetic acid concentration (1800 ppm) in the acrylic acid used in the polymerization, the acetic acid concentration in the water-absorbing resin (S7) thus obtained was 840 ppm, and acetic acid concentration lowering rate was 53.3% (=(1−840/1800)×100).

Example 8

The operation in Example 1 was repeated, except that the time period for blowing the over-heated steam in Example 7 was changed to 20 min, thereby obtaining water-absorbing resin powder (8) and water-absorbing resin (S8).

Temperature of the water-containing gel-like cross-linked polymer in the form of particles after being subjected to the blow of over-heated steam was about 80° C. The water-absorbing resin powder (8) thus obtained was 4.1 wt % in moisture content, 37 g/g in CRC, and 9.7 wt % in water soluble component.

In the steps of the water-absorbing resin manufacturing process herein, acetic acid removing rates were as follows: 12% in the polymerization step (the acetic acid concentration was changed from 630 ppm to 680 ppm against moisture content change from 57 wt % to 47 wt %), 40% in the drying step (the acetic acid concentration was changed from 680 ppm to 740 ppm against moisture content change from 47 wt % to 4.1 wt %), and approximately 0% in the surface crosslinking step (the acetic acid concentration was changed from 740 ppm to 730 ppm against moisture content change from 4.1 wt % to 5.3 wt %), with 47% throughout the overall manufacturing process. Moreover, the acetic acid concentration in the water-absorbing resin (S8) was 730 ppm, and acetic acid concentration lowering rate was 59.4% (=(1−730/1800)×100).

Example 9

The operation in Example 3 was repeated, except that the acrylic acid composition (a4) prepared in Production Example 4 was used, thereby obtaining water-absorbing resin (S9).

Acetic acid removing rates in the steps of the manufacturing process were similar to those in Example 3 with 19% throughout the overall manufacturing process. Moreover, in comparison with the acetic acid concentration (1470 ppm) in the acrylic acid composition (a4), the acetic acid concentration in the water-absorbing resin (S9) was 940 ppm, and acetic acid concentration lowering rate was 36.1% (=(1−940/1470)×100).

Example 10

The operation in Example 8 was repeated, except that the acrylic acid composition (a4) prepared in Production Example 4 was used, thereby obtaining water-absorbing resin (S10).

Acetic acid removing rates in the steps of the water-absorbing resin manufacturing process were similar to those in Example 8 with 47% throughout the overall manufacturing process. Moreover, in comparison with the acetic acid concentration (1470 ppm) in the acrylic acid composition (a4), the acetic acid concentration in the water-absorbing resin (S10) was 600 ppm, and acetic acid concentration lowering rate was 59.2% (=(1−600/1470)×100).

Referential Example 1

A water-absorbing resin was taken out from a diaper (TENA Heavy Protection Underwear) made by SCA, obtained in the USA in December, 2010, and set as control (3 pieces) for odor sensory evaluation.

TABLE 1

| | Acrylic acid composition | | | Water-absorbing resin | | | | | A.A.C. |
|---|---|---|---|---|---|---|---|---|---|
| | Type | Acetic acid [ppm] | Propionic acid [ppm] | Type | Odor S. E. 1 [—] | Odor S. E. 2 [—] | Residual monomer [ppm] | Propionic acid [ppm] | Acetic acid [ppm] | Low. rate [%] |
| Com. Ex. 1 | a3 + ProA | 1200 | 300 | c1 | 3.3 | 2.7 | 530 | 180 | 860 | 28.3 |
| Example 1 | a2 | 1800 | 400 | S1 | 2.4 | 2.7 | 450 | 200 | 1130 | 37.2 |
| Example 2 | a3 | 1200 | 280 | S2 | 3.0 | 2.7 | 450 | 140 | 760 | 35.7 |
| Example 3 | a2 | 1800 | 400 | S3 | 3.3 | 3.0 | 470 | 200 | 1150 | 35.1 |
| Example 4 | a2 | 1800 | 400 | S4 | 3.3 | 2.9 | 470 | 190 | 1150 | 35.1 |
| Example 5 | a2 | 1800 | 400 | S5 | 3.1 | 2.8 | 440 | 180 | 1100 | 38.9 |
| Example 6 | a2 + AcOH | 7000 | 400 | S6 | 3.5 | 2.6 | 440 | 190 | 4420 | 36.9 |
| Com. Ex. 2 | c2 | 12000 | 400 | c2 | 4.3 | 2.6 | 440 | 200 | 7590 | 36.8 |
| Com. Ex. 3 | c3 | 18000 | 400 | c3 | 4.8 | 2.8 | 440 | 200 | 11350 | 36.9 |
| Com. Ex. 4 | c4 | 500 | 12000 | c4 | 3.4 | 3.3 | 190 | 2500 | 250 | 50.0 |

TABLE 1-continued

| | Acrylic acid composition | | | Water-absorbing resin | | | | | A.A.C. |
|---|---|---|---|---|---|---|---|---|---|
| | Type | Acetic acid [ppm] | Propionic acid [ppm] | Type | Odor S. E. 1 [—] | Odor S. E. 2 [—] | Residual monomer [ppm] | Propionic acid [ppm] | Acetic acid [ppm] | Low. rate [%] |
| Com. Ex. 5 | a4 | 500 | 12000 | c5 | 4.5 | 3.5 | 520 | 5500 | 340 | 32.0 |
| Example 7 | a2 | 1800 | 400 | S7 | 3.1 | 2.9 | 330 | 140 | 840 | 53.3 |
| Example 8 | a2 | 1800 | 400 | S8 | 3.1 | 2.9 | 290 | 130 | 730 | 59.4 |
| Example 9 | a4 | 1470 | 270 | S9 | 3.2 | 2.7 | 460 | 140 | 940 | 36.1 |
| Example 10 | a4 | 1470 | 270 | S10 | 3 | 2.8 | 290 | 90 | 600 | 59.2 |
| Ref. Ex. 1 | — | — | — | — | 3.0 | 3.0 | 310 | ND | ND | — |

Com. Ex.: Comparative Example
Ref. Ex.: Referential Example
Odor S.E.: Odor sensory evaluation
A.A.C. Low. rate: Acetic acid concentration lowering rate

TABLE 2

| | | Water-absorbing resin | | | | | | | |
|---|---|---|---|---|---|---|---|---|---|
| | Type | Weight average particle diameter (D50) [μm] | Logarithmic standard deviation ($\sigma\zeta$) [—] | CRC [g/g] | AAP [g/g] | SPC [(1)] | PSR [g/g/s] | Moisture content [wt %] | Internal gas bubbles ratio [—] |
| Com. Ex. 1 | c1 | 410 | 0.43 | 30 | 22 | 41 | 0.23 | 5.1 | 0.3 |
| Example 1 | S1 | 430 | 0.33 | 28 | 22 | 96 | 0.24 | 5.3 | 1.3 |
| Example 2 | S2 | 430 | 0.33 | 27 | 22 | 97 | 0.24 | 5.2 | 1.3 |
| Example 3 | S3 | 430 | 0.33 | 27 | 23 | 121 | 0.24 | 2.3 | 1.3 |
| Example 4 | S4 | 430 | 0.33 | 26 | 23 | 125 | 0.24 | 2.1 | 1.3 |
| Example 5 | S5 | 430 | 0.34 | 26 | 23 | 92 | 0.24 | 7.4 | 1.3 |
| Example 6 | S6 | 430 | 0.34 | 27 | 22 | 94 | 0.24 | 5.3 | 1.4 |
| Com. Ex. 2 | c2 | 430 | 0.34 | 27 | 19 | 86 | 0.24 | 5.2 | 1.4 |
| Com. Ex. 3 | c3 | 430 | 0.34 | 27 | 18 | 83 | 0.24 | 5.3 | 1.5 |
| Com. Ex. 4 | c4 | 490 | 0.31 | 31 | — | — | — | 10.0 | 0.1 |
| Com. Ex. 5 | c5 | 420 | 0.43 | 36 | — | — | — | 5.2 | 2.3 |
| Example 7 | S7 | 430 | 0.34 | 28 | 22 | 94 | 0.24 | 5.3 | 1.5 |
| Example 8 | S8 | 430 | 0.34 | 28 | 22 | 94 | 0.25 | 5.3 | 1.5 |
| Example 9 | S9 | 430 | 0.33 | 27 | 23 | 120 | 0.24 | 2.3 | 1.3 |
| Example 10 | S10 | 430 | 0.34 | 28 | 22 | 94 | 0.25 | 5.3 | 1.6 |
| Ref. Ex. 1 | — | 380 | 0.39 | 32 | 22 | 16 | 0.27 | 5.1 | 0.1 |

(1): $\times 10^{-7} \cdot cm^3 \cdot s \cdot g^{-1}$
Com. Ex.: Comparative Example
Ref. Ex.: Referential Example (Main Points)

In Comparative Example 1, the experiment was carried out in accordance with Example 3 of Patent Literature 12 (U.S. Pat. No. 7,307,132), and the increase in solid content in polymerization was insufficient (i.e., 0%) and the drying temperature was relatively low, i.e., 160° C. Therefore, the acetic acid concentration lowering rate was low (i.e., 28.3%).

The comparative water-absorbing resin powder (4) obtained in Comparative Example 4 showed a water repellent property. This phenomenon indicates that the surfactant remained on the surface of the comparative water-absorbing resin powder (4). Further, the comparative water-absorbing resin powder (4) was in the form of large spherical particles, had an excessively small specific surface area, and showed a low water absorbing speed (FSR).

In Comparative Example 5, the propionic acid concentration in acrylic acid was high and an odor was generated from the obtained comparative water-absorbing resin powder. Moreover, the logarithmic standard deviation ($\sigma\zeta$) of particle size distribution of the water-containing gel-like cross-linked polymer was not controlled and the dewing point in the drying step was low, and therefore the removal of acetic acid was not sufficiently carried out.

On the other hand, in Examples 1 through 6, the increase in solid content in the polymerization was higher, i.e., 10%, and the acetic acid concentration lowering rate was 35% or higher, which was higher than those of Comparative Example 1 and Comparative Example 6, because the particle size of the water-containing gel-like cross-linked polymer, the drying temperature, and the dewing point were controlled. Moreover, by thus controlling the particle size, the amount of fine powder was reduced so that the specific surface area was moderately reduced. The water-absorbing resins, which were thus obtained in Examples 1 through 6, were made up of acrylic acid in which an acetic acid concentration was higher than that of generally used acrylic acid. However, worsening in odor was hardly shown in the odor sensory evaluation, and the water absorbing property, i.e., the liquid permeability was high. Therefore, the water-absorbing resins obtained in Examples 1 through 6 are suitable for a thin diaper and the like.

In Production Example 3 and Example 2, acrylic acids having different acetic acid contents (acetic acid concentrations) were mixed together. Even in a case where acrylic acid containing a high concentration of acetic acid is used, it is possible to sufficiently lower the acetic acid concentration in the water-absorbing resin by combining with the method of the present invention for lowering the acetic acid concentration. Further, this makes it possible to achieve advantage of scale and further leveling of quality, as compared with manufacturing of water-absorbing resin for each of acrylic acids having different acetic acid concentrations.

In Examples 3 and 4, the heat treatment was carried out and additionally the pressure was slightly (i.e., by 0.2%) reduced in the surface crosslinking step. Therefore, acetic acid was removed also in the surface crosslinking step.

The neutralization rate in Example 4 (i.e., 69 mol %) was lower than that of Example 3 (i.e., 75 mol %)). Therefore, the acetic acid concentration lowering rate was slightly increased from 36.1% to 37.2%. This may be because the decrease in neutralization rate inhibited acetic acid from becoming acetic acid salt and evaporation easily occurred.

In Comparative Examples 2 and 3, the acetic acid concentration lowering rate was approximately 37%. However, the acetic acid concentration in acrylic acid was higher than 10000 ppm, and therefore the obtained water-absorbing resin had problems of not only odor but also deterioration in water absorbing property (AAP, SFC).

In Example 6, the odor sensory evaluation 1 and the odor sensory evaluation 2 were carried out simultaneously, and the degree of odor evaluated in the odor sensory evaluation 2 was lower than that of the odor sensory evaluation 1. This may be because the ammonia odor, which was derived due to ammonium salt contained in the absorbed liquid used in the odor sensory evaluation 2, was combined with odor of the acetic acid which was contained by 4420 ppm in the water-absorbing resin powder (6) of Example 6, and the ammonia odor and the acetic acid odor canceled each other out.

In Examples 7 and 8, the hydrogel is exposed to steam so as to have higher humidity than Examples 1 through 6. Therefore, acetic acid was efficiently removed, and the acetic acid concentration lowering rate was improved.

In Examples 9 and 10, acrylic acid was used whose acetic acid concentration was higher, by 5 times or more, than propionic acid concentration by crystallization, that is, the propionic acid concentration was originally low. The acetic acid removing rate, the acetic acid concentration lowering rate, and water absorbing properties of the obtained water-absorbing resin were substantially identical with those in the case where acrylic acid obtained by distillation was used.

In Comparative Example 1, the average sphericity of the comparative water-absorbing resin (c1) was 0.67. In Comparative Example 4, the average sphericity of the comparative water-absorbing resin (c4) was 0.66. In Comparative Example 5, the average sphericity of the comparative water-absorbing resin (c5) was 0.95. In Examples 1 through 8, the average sphericities of the water-absorbing resins were in a range of 0.70 to 0.72.

The present invention is not limited to the embodiments, but can be altered by a skilled person in the art within the scope of the claims. An embodiment derived from a proper combination of technical means disclosed in respective different embodiments is also encompassed in the technical scope of the present invention.

INDUSTRIAL APPLICABILITY

The method of the present invention for manufacturing polyacrylic acid (salt)-based water-absorbing resin is applicable to production, in particular, mass production of water-absorbing resin. Moreover, the polyacrylic acid (salt)-based water-absorbing resin obtained by the present invention is suitable for an absorbent body of hygiene product such as a disposable diaper.

The invention claimed is:

1. A method for manufacturing a polyacrylic acid (salt)-based water-absorbing resin, said method comprising the steps of:
   (a) preparing a monomer aqueous solution containing acrylic acid (salt) as a main component;
   (b) obtaining a water-containing gel-like cross-linked polymer by carrying out aqueous solution polymerization or spray drop polymerization with the monomer aqueous solution;
   (c) drying the water-containing gel-like cross-linked polymer; and
   (d) surface-crosslinking water-absorbing resin powder obtained after the step (c),
   the steps (a) through (d) being carried out in this order,
   an acetic acid concentration in acrylic acid or an acrylic acid aqueous solution, which is supplied in the step (a), being in a range of 300 ppm to 10000 ppm (on an acrylic acid basis),
   in the acrylic acid or the acrylic acid aqueous solution, the acetic acid concentration (ppm) is higher than a propionic acid concentration (ppm) by 3 times or more and
   an acetic acid concentration lowering rate, which is defined by Formula 1 below, being 35% or higher:

[Math. 1]

(Acetic acid concentration lowering rate) (%)={1−(acetic acid concentration (ppm) in water-absorbing resin)/(acetic acid concentration (on acrylic acid basis) (ppm) in acrylic acid or acrylic acid aqueous solution)}×100    Formula 1 where "(acetic acid concentration (ppm) in water-absorbing resin)" is an acetic acid concentration in the polyacrylic acid (salt)-based water-absorbing resin, and "(acetic acid concentration (on acrylic acid basis) (ppm) in acrylic acid or acrylic acid aqueous solution)" is an acetic acid concentration (on the acrylic acid basis) (ppm) in the acrylic acid or the acrylic acid aqueous solution which is supplied in the step (a).

2. The method as set forth in claim 1, wherein:
   the polymerization is foaming polymerization or grain refining polymerization in which the monomer aqueous solution has a concentration of solid content in a range of 30 wt % to 55 wt % and a degree of increase in solid content in the monomer aqueous solution is in a range of 1 wt % to 15 wt %; and
   acetic acid contained in the monomer aqueous solution is at least partially removed in the step (b).

3. The method as set forth in claim 1, wherein:
   the polymerization is carried out on the monomer aqueous solution which has a concentration of solid content of lower than 30 wt %; and
   in and/or after the step (b), said method further comprises the step of neutralizing the water-containing gel-like cross-linked polymer.

4. The method as set forth in claim 1, wherein:
   the water-containing gel-like cross-linked polymer, which is subjected to the step (c), is such that a weight average particle diameter (D50) of the water-containing gel-like cross-linked polymer is in a range of 350 μm to 2000 μm, and a logarithmic standard deviation (σζ) of particle size distribution of the water-containing gel-like cross-linked polymer is in a range of 0.2 to 1.5.

5. The method as set forth in any claim 1, wherein:
   in the step (c), acetic acid contained in the water-containing gel-like cross-linked polymer, whose concentration of solid content is 50 wt % or lower, is at least partially removed by drying the water-containing gel-like cross-linked polymer by hot air.

6. The method as set forth in claim 1, wherein:
in the step (c), acetic acid contained in the water-containing gel-like cross-linked polymer is at least partially removed by adding a drying aid to the water-containing gel-like cross-linked polymer.

7. The method as set forth in claim 1, wherein:
in the step (c), acetic acid contained in the water-containing gel-like cross-linked polymer is at least partially removed by drying the water-containing gel-like cross-linked polymer at a drying temperature in a range of 165° C. to 230° C. for 5 minutes or more.

8. The method as set forth in claim 1, wherein:
in the step (c), acetic acid contained in the water-containing gel-like cross-linked polymer is at least partially removed (i) by controlling an ambient dewing point to be in a range of 50° C. to 100° C. during 50% or more of drying time or (ii) by reducing a pressure by 0.1% to 5% with respect to an atmospheric pressure during 50% or more of drying time.

9. The method as set forth in claim 1, further comprising the step of: (e) carrying out pulverization with use of a multiple-stage roll mill after the step (c).

10. The method as set forth in claim 1, wherein:
in the step (d), acetic acid contained in the water-absorbing resin powder is at least partially removed by surface-crosslinking the water-absorbing resin powder in the presence of an acidic compound.

11. The method as set forth in claim 1, wherein:
in the step (d), acetic acid contained in the water-absorbing resin powder is at least partially removed by adding a surface crosslinking agent solution and then reducing the pressure by 0.1% to 5% with respect to the atmospheric pressure during 50% or more of heat treatment time.

12. The method as set forth in claim 1, further comprising the step of:
(f) remoistening the water-absorbing resin, which has been obtained after the step (d), by carrying out heat treatment after adding 0.5 part by weight to 15 parts by weight of water to 100 parts by weight of the water-absorbing resin.

13. The method as set forth in claim 12, wherein:
in the step (f), a polyvalent metal ion is added.

14. The method as set forth in claim 12, wherein:
in the step (f), acetic acid is at least partially removed by maintaining the water-absorbing resin, which has been remoistened, at a temperature in a range of 65° C. to 99° C. for 5 minutes or more.

15. The method as set forth in claim 12, wherein:
in the step (f), a moisture content in the water-absorbing resin is controlled to be in a range of 2 wt % to 9 wt %.

16. The method as set forth in claim 1, wherein:
an acetic acid concentration in the polyacrylic acid (salt)-based water-absorbing resin is in a range of 100 ppm to 7000 ppm.

17. The method as set forth in claim 1, wherein:
acetic acid contained in the acrylic acid or the acrylic acid aqueous solution supplied in the step (a) is removed in and/or after the step (b) so that an acetic acid removing rate defined by Formula 2 below becomes 10% or higher:

[Math. 2]

(Acetic acid removing rate) (%)={1−(acetic acid concentration after processing) (ppm)×(weight of water-absorbing resin after processing) (g)/(acetic acid concentration before processing) (ppm)× (weight of water-absorbing resin before processing) (g)}×100     Formula 2.

18. The method as set forth in claim 1, wherein:
in the acrylic acid or the acrylic acid aqueous solution, the acetic acid concentration is in a range of 1300 ppm to 10000 ppm, and the propionic acid concentration is 400 ppm or lower.

19. The method as set forth in claim 1, wherein:
acetic acid is removed by causing an acetic acid-containing exhaust gas, which has been generated, to make contact with an alkaline liquid so that acetic acid is absorbed by the alkaline liquid.

20. The method as set forth in claim 1, wherein:
the acrylic acid or the acrylic acid aqueous solution is a mixture of two or more types of acrylic acid or acrylic acid aqueous solution which are different in acetic acid concentration.

21. The method as set forth in claim 1, wherein:
in the acrylic acid or the acrylic acid aqueous solution, an amount of methoxyphenols is in a range of 10 ppm to 160 ppm, an amount of an acrylic acid dimer is 1000 ppm or less, an amount of protoanemonin (PAN) is 5 ppm or less, an amount of an aldehyde content is 5 ppm or less, and a total amount of allyl acrylate and allyl alcohol is 20 ppm or less.

22. A polyacrylic acid (salt)-based water-absorbing resin, wherein:
an acetic acid concentration is in a range of 100 ppm to 7000 ppm, a propionic acid concentration is less than 300 ppm, a residual monomer concentration is less than 500 ppm, a weight average particle diameter (D50) is in a range of 300 μm to 600 μm, and a logarithmic standard deviation (σζ) of particle size distribution is in a range of 0.20 to 0.50, and the acetic acid concentration (ppm) is higher than the propionic acid concentration (ppm) by 3 times or more.

23. The polyacrylic acid (salt)-based water-absorbing resin as set forth in claim 22, wherein:
an internal gas bubbles ratio is in a range of 0.1% to 3.0%, and a water absorbing speed (FSR) is in a range of 0.10 to 0.40 (g/g/s).

24. The polyacrylic acid (salt)-based water-absorbing resin as set forth in claim 22, wherein:
a saline flow conductivity (SFC) is $50[\times 10^{-7} \cdot s \cdot cm^3 \cdot g^{-1}]$ or higher.

25. The polyacrylic acid (salt)-based water-absorbing resin as set forth in claim 22, wherein a sphericity is 0.65 or higher.

26. The polyacrylic acid (salt)-based water-absorbing resin as set forth in claim 22, wherein:
the polyacrylic acid (salt) is polyacrylic acid sodium salt whose neutralization rate is 10 mol % or higher and lower than 90 mol %.

* * * * *